(12) United States Patent
Fiekowsky

(10) Patent No.: US 6,397,165 B1
(45) Date of Patent: May 28, 2002

(54) MICROSCOPIC CORNER RADIUS MEASUREMENT SYSTEM

(75) Inventor: Peter J. Fiekowsky, 952 S. Springer Rd., Los Altos, CA (US) 94024

(73) Assignee: Peter J. Fiekowsky, Los Altos, CA (US)

( * ) Notice: Subject to any disclaimer, the term of this patent is extended or adjusted under 35 U.S.C. 154(b) by 0 days.

(21) Appl. No.: 09/877,647

(22) Filed: Jun. 7, 2001

Related U.S. Application Data

(63) Continuation-in-part of application No. 09/028,207, filed on Feb. 23, 1998, now Pat. No. 6,263,292, which is a continuation-in-part of application No. 08/807,789, filed on Feb. 28, 1997, now Pat. No. 5,966,677.

(51) Int. Cl.⁷ .............................................. G03B 27/42
(52) U.S. Cl. ......................... 702/157; 702/159; 702/95; 356/241
(58) Field of Search ................................. 702/157, 159, 702/95; 348/128; 356/241, 254, 429, 430; 355/53, 67–69

(56) References Cited

U.S. PATENT DOCUMENTS

| | | | |
|---|---|---|---|
| 5,477,332 A | * 12/1995 | Stone et al. ................. | 348/128 |
| 5,614,990 A | 3/1997 | Bruce et al. ................. | 355/71 |
| 5,804,336 A | 9/1998 | Rolfon ........................... | 430/5 |
| 5,966,677 A | 10/1999 | Fiekowsky .................... | 702/95 |
| 6,127,071 A | * 10/2000 | Lu .............................. | 430/30 |
| 6,263,292 B1 | * 7/2001 | Fiekowsky .................. | 702/159 |

OTHER PUBLICATIONS

George et al., "A Practical and Precise Method for Mask Defect Size Measurement," Mar. 10, 1996, Proceedings of the SPIE Conference on Photo–Lithography.
Stocker et al., "Characterization of Defect Sizing on an Automatic Inspection Station (KLA–238e)," 1993, SPIE vol. 2087 Photomask Technology and Management.
Karvahira et al., "SEMI Standards Programmed Defect Masks and its Applications for defect Inspection", SEMI JAPAN Standards Committee.
Peter J. Fiekowsky, Quotation (Preliminary), Oct. 17, 1994.
Fiekowsky et al., "Defect Printability Measurement on the KLA–351: Correlation to Defect Sizing Using the AVI Metrology System", SPIE $19_{th}$ Annual BACUS Symposium on Photomask Technology and Management Conference 3873, Sep. 1999.
Tran et al., "Application of Image processing Software to Characterize the Photomask Key Parameters for Future Technologies," Apr. 17–18, 1997, Proceedings of SPIE vol. 3096.

\* cited by examiner

*Primary Examiner*—Kamini Shah
(74) *Attorney, Agent, or Firm*—Beyer Weaver & Thomas, LLP

(57) ABSTRACT

A measurement tool connects to a microscope for identifying and measuring microscopic dimensions of features on a photographic mask such as area, diameter and corner radius. Dimensions of features having sizes of less than about twice the wavelength being used (less than 1 micron for visible light) are measured quickly and accurately. The radius of curvature is also determined at submicron sizes using a flux measurement. Determination of the expected flux of a perfect corner aids in the measurement.

10 Claims, 23 Drawing Sheets

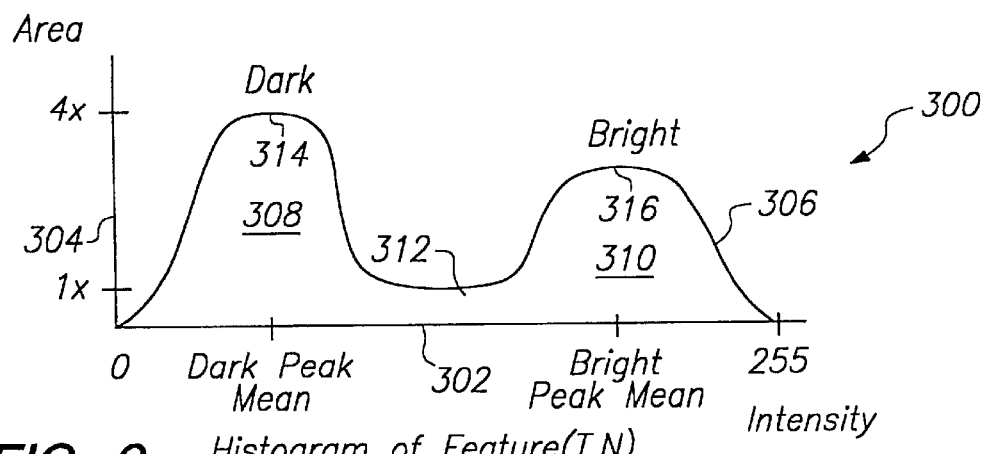
FIG. 9 Histogram of Feature(T,N)
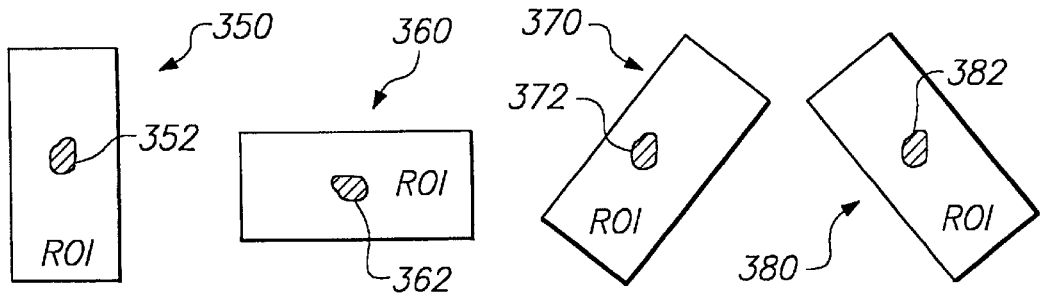
FIG. 10A   FIG. 10B   FIG. 10C   FIG. 10D
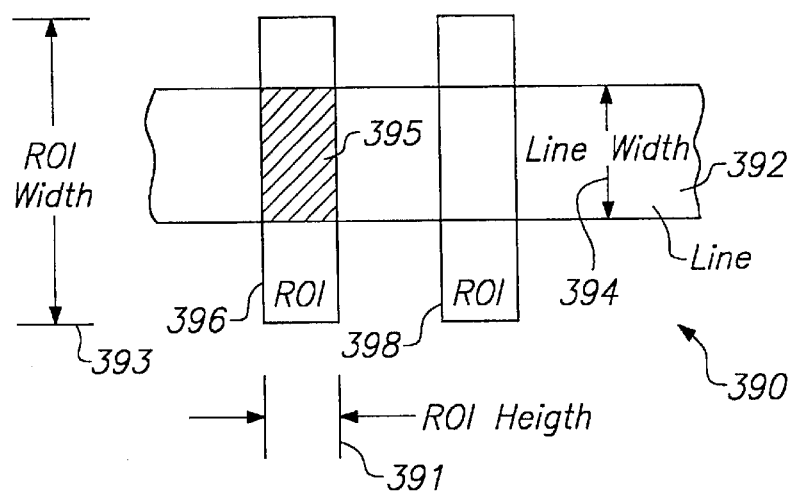
FIG. 10E

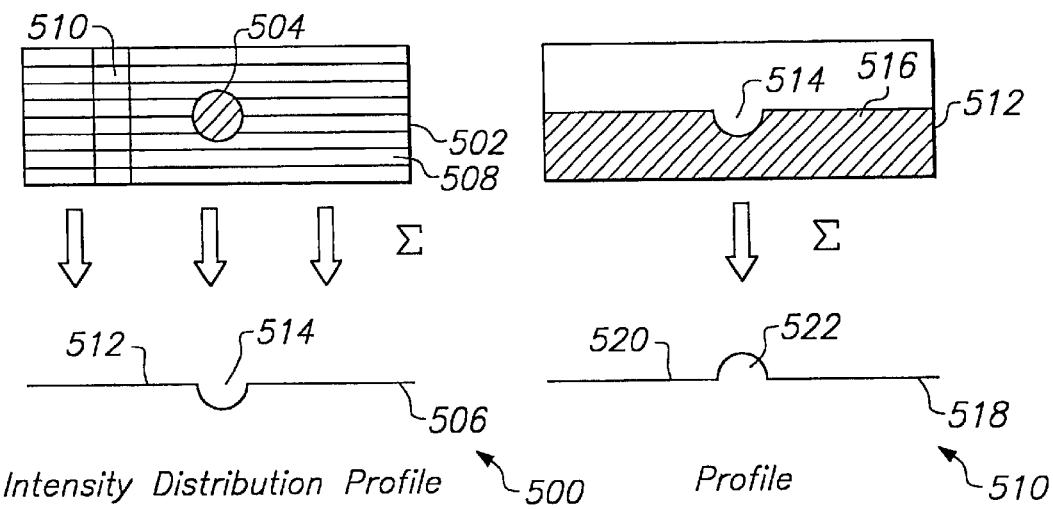
FIG. 11A  FIG. 11B
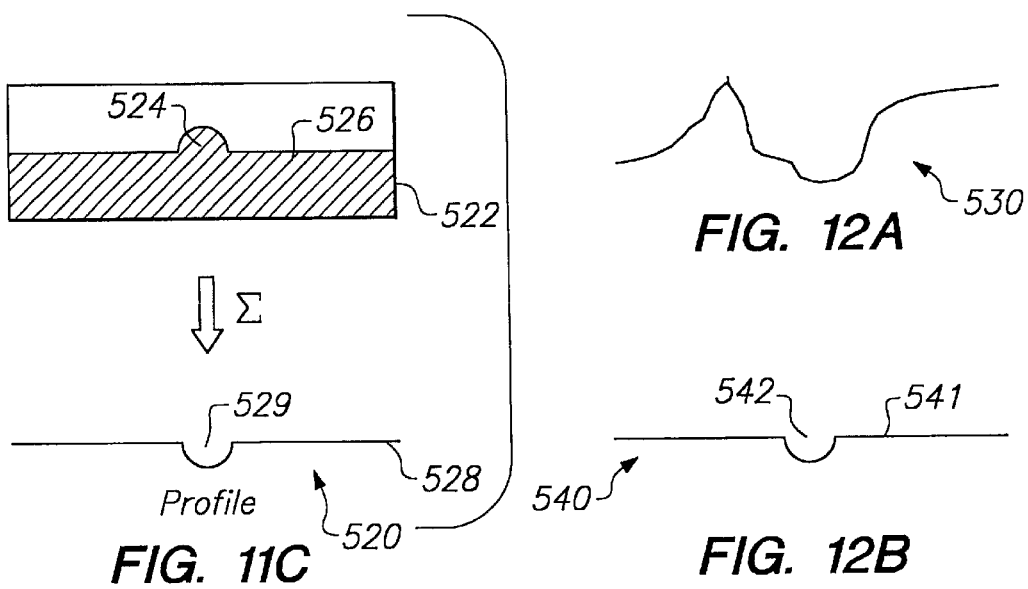
FIG. 11C  FIG. 12A / FIG. 12B
FIG. 12C
FIG. 12D

MICROSCOPIC CORNER RADIUS MEASUREMENT SYSTEM

This application is a continuation-in-part of U.S. patent application Ser. No. 09/028,207 filed on Feb. 23, 1998 now U.S. Pat. No. 6,263,292, which in turns continuation-in-part of U.S. patent Ser. No. 08/807,789 filed on Feb. 28, 1997, now U.S. Pat. No. 5,966,677, both of which are incorporated by reference.

FIELD OF THE INVENTION

The present invention relates generally to computer measurement systems. More specifically, the present invention relates to the measurement of features on photographic masks used in semiconductor manufacturing.

BACKGROUND OF THE INVENTION

The recent introduction of advanced sub-micron sized semiconductor devices require reduced critical dimensions and increased packing densities. At these sub-micron sizes and high densities, even defects and imperfections as small as 1 micron and below are problematic and need to be detected and evaluated. Imperfections in the reticle generated by a photographic ("photomask") mask manufacturing process are one source of defects. Errors generated by such a photomask manufacturing process have become an important issue in the manufacture of semiconductor devices at these sub-micron sizes. Defect inspection techniques for masks are therefore becoming to play a more important role in mask making and quality assurance.

Thus, it is becoming increasingly important to be able to identify and to correctly size mask features that are under 1 micron in size. Accurate sizing of these features allows masks that are below specification to be repaired, and prevents the needless and costly hold up of masks that do meet specification. However, one of the problems of assessing reticle quality at these sub-micron levels on an automatic inspection system is that the size of these features cannot always be accurately, quickly and cost-effectively measured in a production environment. For example, as the line width on sub-micron masks approaches 0.1 micron, the ability to measure feature sizes at 1 micron and below becomes very important. Current production machines have an accuracy of 0.1 micron to 0.2 micron, but this is not sufficient.

It has long been known that mask inspection tools are not measurement tools and that the size information provided by these tools has limited value. Consequently, many mask makers have incorporated measurement aids at the inspection station or have moved the mask to a more suitable measurement tool in order to make classification decisions. Measurement aids used at the inspection station include calipers, grids, and software based video image markers such as gates, scales, grids, boxes and circles. These aids are fairly rapid, but ultimately require the operator to "eyeball" the boundaries of the feature. This activity is very subjective and can lead to an error in the measurement of the feature.

For example, particle size is conventionally measured by measuring the distance between opposite edges of the particle. Once a feature is identified by an inspection machine, the operator uses a video microscope and a television camera to position a cursor on one side of the feature and another cursor on the other side of the feature. The operator must judge for himself the exact boundaries of the feature and must place the cursors where he sees fit. At this point, the operator pushes a button and the software blindly computes the distance between the two cursors in order to supply a rough approximation of the diameter of the feature. This technique is not optimal.

Firstly, this measurement technique is operator dependent in that the operator must manually position the cursors on the boundaries of what the operator believes to be the feature. The operator may misjudge the type of a feature, its boundaries, or may simply misplace a cursor even if the feature is visible. The software then blindly calculates the distance between the cursors, without regard for the type of feature, its true boundaries, etc. The above technique may be performed with a standard video microscope and has an accuracy of about 0.1 micron, but is completely subject to the operator's skill level and interpretation.

Another difficulty with light measurements of features less than 1 micron in size is that the wavelength of photons begins to interfere with the measurement of these smaller and smaller feature sizes. Current techniques do not adequately address the non-linearities associated with such measurements.

Alternatively, the mask may be removed from the automatic inspection tool and relocated on a more precise and repeatable measurement tool. However, this approach involves removing the mask from production, relocating the feature, and is thus impractical in a production environment. This technique is also costly, time-consuming and increases the handling risk. For example, an atomic force microscope (AFM) may be used to measure feature sizes; such a microscope is extremely accurate but is very slow, very expensive and is still subject to operator interpretation.

Therefore, an objective feature measurement tool is desirable for use with a photomask inspection tool that can provide reliable and repeatable measurements of features of less than about one to two times the microscope resolution (or about less than one micron for optical microscopes). It would be especially desirably for such a tool to operate in a fast and highly practical manner in a production environment. More specifically, it would be desirable to be able to determine the radius of curvature of a corner of a line, especially at sizes that approach, or are less than, the wavelength of light or the particle beam being used where blurring is a problem.

SUMMARY OF THE INVENTION

The present invention discloses a measurement tool that provides an objective, practical and fast method for accurate sizing of mask features found with an automatic inspection tool (such as a video inspection machine). Dimensions can be measured by using gray scale image information provided by the automatic inspection tool. The present invention may be used while the photomask is in-place at the inspection station, and there is no need for the mask to be removed to a different machine for measurement. The dimension of the feature is then automatically identified and measured quickly by the measurement tool of the present invention.

Benefits include avoiding repairing masks within specification, and equivalent results whether measured by customer or supplier (when calibrated with the same reference). Operator productivity and tool utilization is improved by rapid measurements taking place at the inspection station.

The disclosed measurement tool objectively and repeatedly measures the radius of curvature of mask features for characterizing photomask quality. The measurement tool operates automatically and is not dependent upon operator judgment. Corner radii from 0.1 to 1.0 microns can be measured, repeatable to 0.02 microns and accurate to 0.05 microns with a typical SEM calibration. Additionally, the measurement tool provides automatic measurements in 1 to 5 seconds (including operator actions).

The disclosure provides a variety of techniques useful for implementing the present invention. In one technique, multiple regions of interest are formed surrounding a feature and an intensity profile is developed for each region of interest. A total light flux measurement is calculated for each profile, and one of the light flux measurements is chosen as the best flux value. A good quality profile is chosen such that the total flux measured from the profile is proportional to the area of the feature. Multiple regions allow for angled lines. A region of interest surrounds the feature and a profile for the feature is produced by summing columns of pixels across the feature site in the region of interest. A baseline intensity value is determined for the profile and is subtracted from the profile in order to determine the total flux passing through the feature. Subtraction of a baseline removes background intensities and obviates the need to obtain a reference image.

In the specific embodiment disclosed, the present invention is able to accurately determine the radius of curvature of corners of features on a variety of media, and especially at subresolution sizes.

Thus, by providing an extremely accurate measurement of mask features, the disclosed measurement tool helps to avoid unnecessary mask repairs and allows for improved process control. Also, operator variability is eliminated, and overall productivity and mask throughput is increased due to the accurate measurements in-place and documentation produced in seconds. Because the measurements are automatic, operator training is minimal.

The present invention is also able to measure specific dimensions of features that are under about one to two times the microscope resolution. Features can all be accurately sized at this subresolution size even though blurring is present. The prior art has had difficulties in measuring the dimension of a feature at subresolution sizes. Frequent reference is made herein to the applicability of the invention for sizes of features less than about 1 micron; this range applies to visible light, where the wavelength is about 0.5 micron. For other wavelengths, the present invention is generally suitable for features having sizes less than about two times the blur distance of the optics being used, or for features that are less than about twice the wavelength being used. The invention is especially suited for features having sizes close to or less than the wavelength being used.

BRIEF DESCRIPTION OF THE DRAWINGS

The invention, together with further advantages thereof, may best be understood by reference to the following description taken in conjunction with the accompanying drawings in which:

FIG. 9 is a graph showing a histogram for a particular feature of a mask.

FIGS. 10A through 10D show various orientations for system regions of interest that surround a particular defect.

FIG. 10E shows two system regions of interest used for developing profiles of a line width.

FIGS. 11A through 11C illustrate how a system region of interest of a flux source image may be summed in order to create an intensity distribution profile for a particular feature.

FIGS. 12A through 12D illustrate possible resulting intensity profiles for the flux source image of FIG. 11A depending upon the orientation of the system regions of interest used.

DETAILED DESCRIPTION OF THE INVENTION

In one embodiment of the present invention, a number of artificially produced standard features of known sizes are each measured using the measurement tool of the present invention to produce a calibration graph for each type of feature that plots the measured dimension of the feature in pixels versus the known size of the feature in microns. For each type of feature, a number of features of the same type of different sizes are analyzed in order to produce a plot fit with a polynomial curve. These artificial features may be measured in order to determine their true size by using a wide variety of techniques. By way of example, an atomic force microscope, Vickers machine or other may be used to determine the true reference size of the features.

Once the calibration graphs have been developed for each type of feature, then a particular real feature of unknown size is measured using the measurement tool of the present invention. The amount of light absorbed by the feature, or transmitted by a hole in a surface that should be opaque, is measured. This flux value is used to produce an area in pixels of the feature which can then be correlated to the actual reference size in microns of the feature by using the polynomial curve of the previously developed calibration graph for that feature type. In most cases for features smaller than 1 micron, it can be assumed that the feature is effectively circular, thus, the diameter of the feature can be computed from its area. This assumption can be justified because defects smaller than 1 micron will most often appear circular due to the defraction of light (light photons are approximately 0.5 microns in size). Additionally, such defects are typically nearly circular. Defects that are non-circular (and usually larger than 1 micron) can still be measured using the "eyeball" method with the aid of a built-in 1 micron reticle reference grid supplied. Additionally, defects that are not quite opaque are treated as if they were opaque.

A variety of lighting techniques and/or particle microscopes (such as an electron microscope) may be used with the present invention. For illustrative purposes, the present invention is described herein in connection with transmitted illumination, although the applicability of the invention is not so limited.

Overall System

Figure 1:
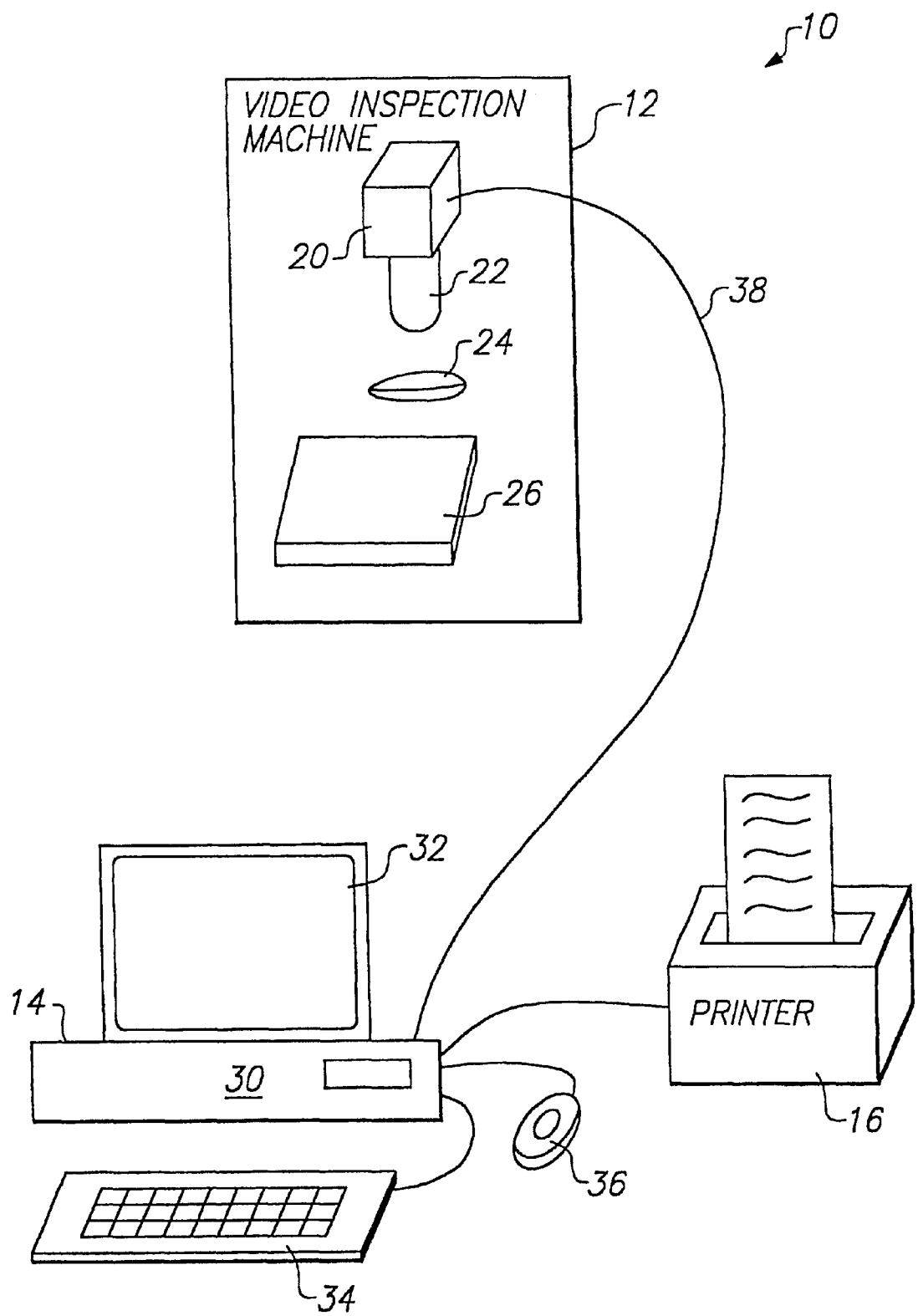
FIG. 1 illustrates a measurement system in accordance with one embodiment of the present invention.

Turning now to FIG. 1, a feature measurement system 10 in accordance with one embodiment of the present invention includes a video inspection machine 12, a computer system 14 and a printer 16. Video inspection machine 12 may be one of a wide variety of automatic inspection tools that analyze microscopic particles, lines, dimensions, etc., and outputs a video image of the microscopic features that it is analyzing. By way of example, machine 12 may be a KLA 2xx or 3xx, or DRS-1, DRS-2 automatic inspection tool used for inspecting photographic masks that are used in the manufacture of semiconductor devices. Machine 12 includes a video camera 20 having a lens tube 22 and a lens 24 that is inspecting a medium 26. Medium 26 may be one of a wide variety of media having microscopic features that are suitable for measurement by the present invention. By way of example, medium 26 is a glass reticle having a chrome pattern upon it forming a mask used in semiconductor manufacturing. Of course, other materials and substrates may be used to form the pattern of the mask. And a wide variety of other media may be suitable for use with present invention. For example, media such as a printed circuit board, other transparent media, and other types of masks may have measurements performed upon them using any of the various techniques of the present invention.

In one embodiment, a multi-camera option may be used in which two or more inspection machines of different types provide video data to the measurement tool. Each machine may use separate calibration data which is changed automatically when input is switched to originate from that machine.

Computer system 14 may be any suitable computer system for embodying the measurement tool of the present invention. By way of example, computer system 14 may be a PC computer having hardware 30, a high resolution monitor 32, a keyboard 34 and a mouse or track ball 36. Printer 16 is also connected to computer system 14 for allowing results of feature measurements to be printed.

Computer system 14 is connected to machine 12 via cable 38 which may be any suitable cable for transmitting raw video output data from machine 12 to computer system 14. In operation, machine 12 transmits via cable 38 multiplexed (in time or by position) feature image data and reference data to computer 14 for analysis and measurement. The reference data received from machine 12 is an image of what a particular portion of the mask should look like free of defects. This reference data may be retrieved from a mask database or may be obtained by doing a die to die comparison. Reference data is used when a good quality profile is difficult to obtain and will be explained in greater detail below with reference to FIG. 7. Thus, machine 12 transmits not only the results of measuring artificially produced standard features for the purpose of producing calibration data, but also transmits live video images and reference images for actual features of unknown dimensions that are identified upon mask 26.

Figure 2:
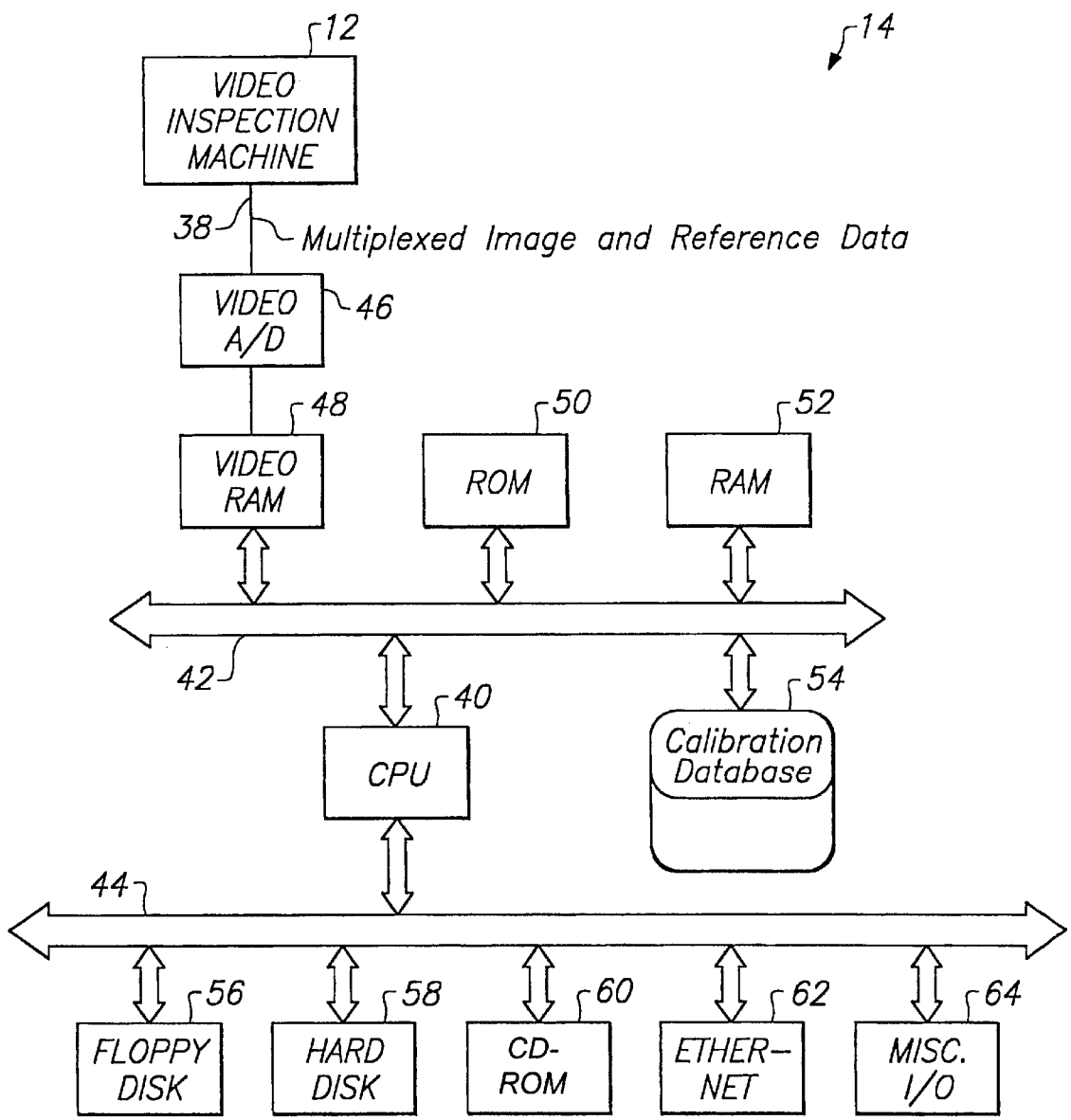
FIG. 2 is a block diagram of an embodiment of a computer system used in the measurement system of FIG. 1.

FIG. 2 illustrates in greater detail the computer system 14 of FIG. 1. A wide variety of computer configurations may be used; one alternative embodiment for a computer system 14 is shown in a later figure. Hardware 30 includes a CPU 40 connected to a PCI bus 42 and also connected to any suitable computer bus 44. Video data from machine 12 travels over cable 38 to digitizer hardware 46 that converts the video analog signal to digital form. Hardware 46 is preferably high-resolution video capture hardware.

Figure 17:
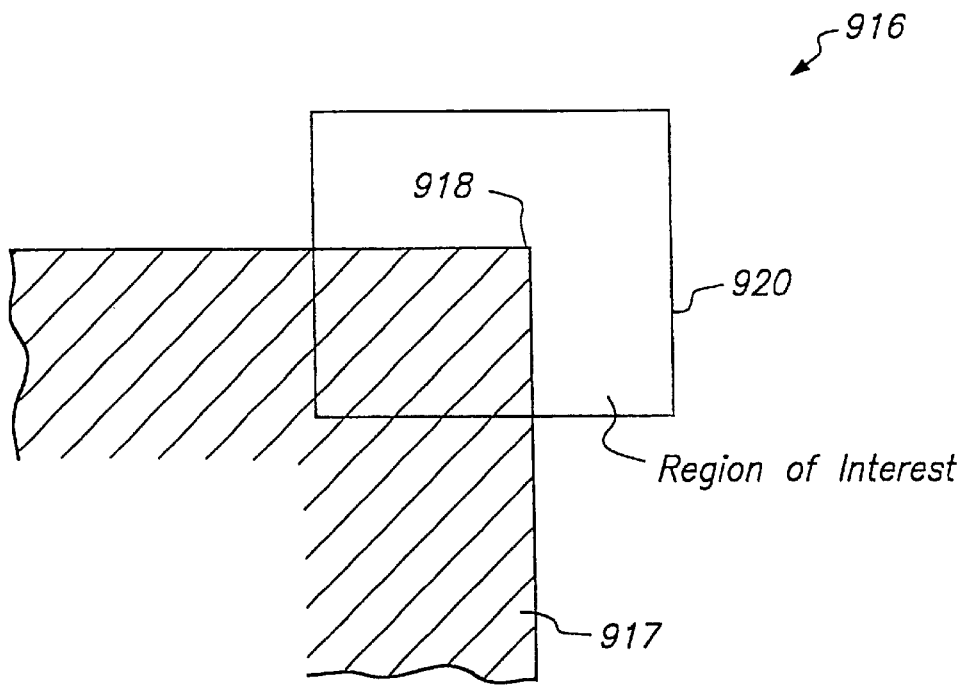
FIG. 17 illustrates a reference corner useful in determining the radius of curvature of an actual corner.
Figure 18:
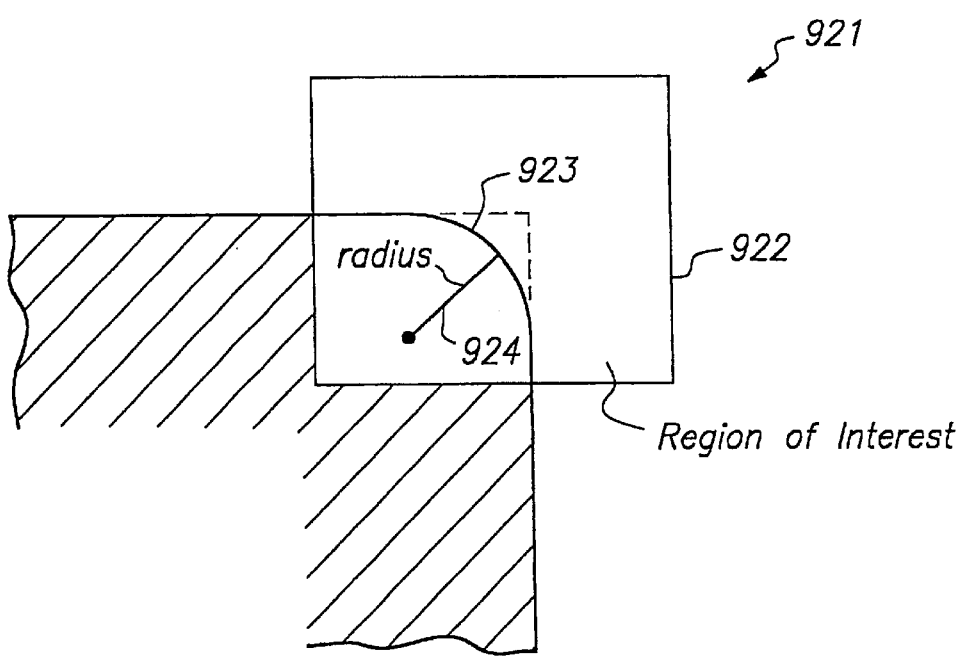
FIG. 18 illustrates an actual corner and its radius of curvature.

Once the video data has been converted to digital form by digitizer 46 the digital data is stored in video ram 48. Also connected to bus 42 is read-only memory (ROM) 50 and random access memory (RAM) 52. A calibration database 54 is also accessible via bus 42 and may be contained in any suitable memory of the computer. Calibration database 54 contains individual points plotted as shown in FIGS. 16, 17 and 18, and also the equations for the polynomial curves that represent these points. The database will be explained in greater detail below with reference to FIG. 4.

Connected to bus 44 are a wide variety of input and output devices. By way of example, shown are a floppy disk 56, a hard disk 58, a CD-ROM 60, a network connection 62 in the form of an Ethernet connection, and a wide variety of other miscellaneous input and output devices 64 that include printer 16, monitor 32, keyboard 34 and track ball 36.

Features, Defects and Line Widths

The measurement system of the present invention is suitable for identifying and measuring a variety of features such as defects and line widths present on a photographic mask. A wide variety of defects may appear during the manufacture of the mask. FIGS. 3A through 3E illustrate examples of types of defects and a line width. Defects include isolated defects such as spots or holes, edge defects such as extensions and intrusions, and a wide variety of other types of defects. Other features that may be measured include the width of a chrome line or the width of spacing between such lines.

Figure 3A:
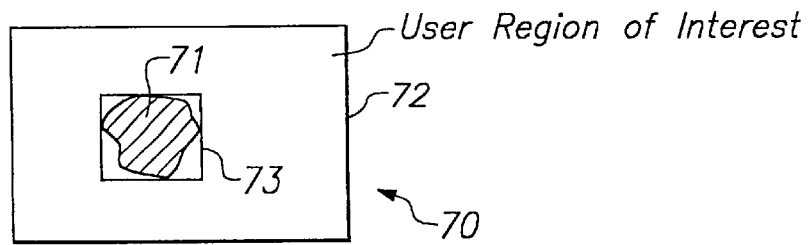
FIGS. 3A through 3E illustrate various features of a photographic mask each surrounded by a user region of interest.

FIG. 3A shows a feature site 70 to be measured. Feature site 70 includes a spot defect 71 surrounded generally by a user region of interest 72. A bounding box 73 bounds spot 71. A spot defect occurs when a particle of chrome or other contaminant is present by itself in location where it does not belong. As will be explained in greater detail below with reference to FIG. 4, when inspection machine 12 identifies a feature such as spot 71, the operator is able to enter review mode and to quickly surround spot 71 with a rough user region of interest 72 indicating the region that the user wishes to analyze and measure. Advantageously, the operator need only roughly draw a rough user region of interest around spot 71, and need not judge for himself the exact boundaries of the defect. Bounding box 73 is created by the measurement tool in order to determine the type of feature that the user has chosen to measure and will be explained in greater detail below with reference to FIG. 7B.

Figure 3B:
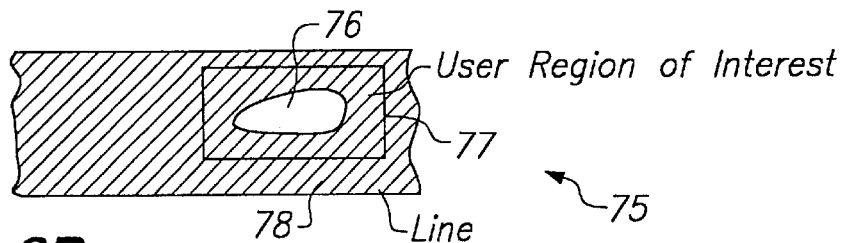
Figure 3C:
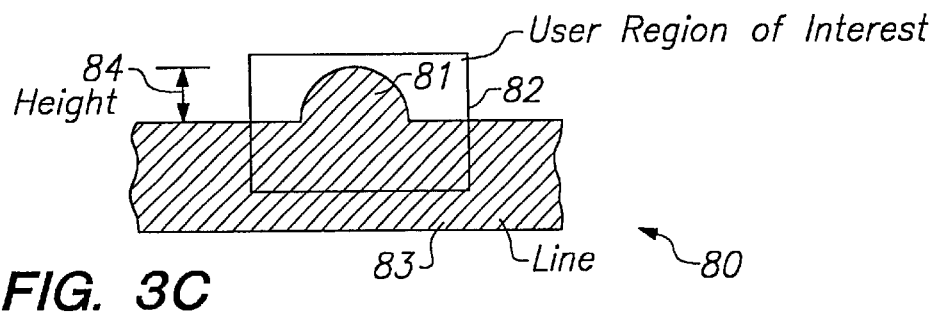
Figure 3D:
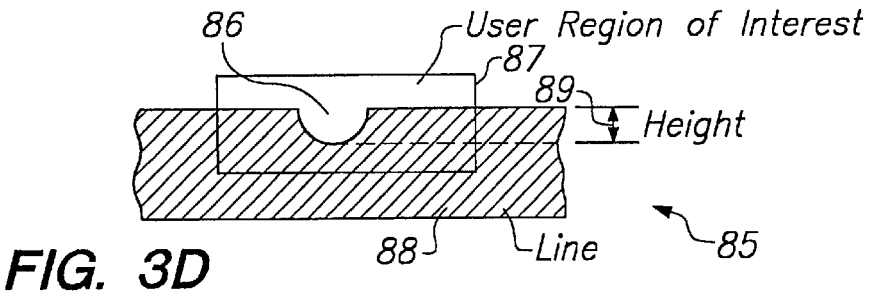

FIG. 3B shows a feature site 75 in which a line 78 has a hole defect 76. Hole 76 is surrounded by a user region of interest 77. A hole may occur when a section of a chrome line (for example) is lacking a piece of chrome such that a hole appears. FIG. 3C shows a feature site 80 in which a line 83 has an extension edge defect 81. This defect is surrounded by a user region of interest 82. An extension edge defect occurs when a portion of a line extends, or bulges out away from the line and is convex in shape. By convention, the height 84 of the extension refers to how far the defect extends from line 83. FIG. 3D shows a feature site 85 in which a line 88 has an intrusion edge defect 86. This defect is surrounded by a user region of interest 87. An intrusion edge defect occurs when a portion of a line is missing along an edge and has a concave shape. By convention, the height 89 of the intrusion refers to how far the defect intrudes into line 88.

Figure 3E:
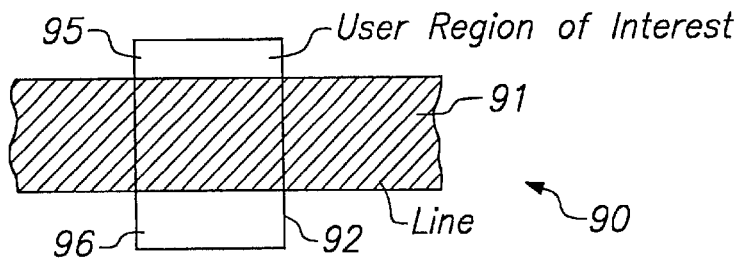

FIG. 3E shows a feature site 90 in which the width of line 91 is desired to be measured. A user region of interest 92 encompasses the width of line 91. Line 91 may be an opaque line, a transmissive clear region between lines, or other. As will be explained in greater detail below with reference to FIG. 7B, line 91 presents a dark region surrounded on either side by bright regions 95 and 96. With each of these defects and features, the operator is able to easily and quickly draw a user region of interest around the feature site to be measured and need not exercise any judgement regarding the size of the feature.

A wide variety of other types of defects and features such as dots, protrusions, corner defects, bridges, truncations, misplacements, half-tones, etc., as described in "SEMI Standards Programmed Defect Masks and Its Applications for Defect Inspection", by H. Kawahira and Y. Suzuki, SEMI Japan Standards Committee, Mountain View, Calif., may be analyzed and measured using the invention disclosed herein.

Calibration Curves

Figure 4:
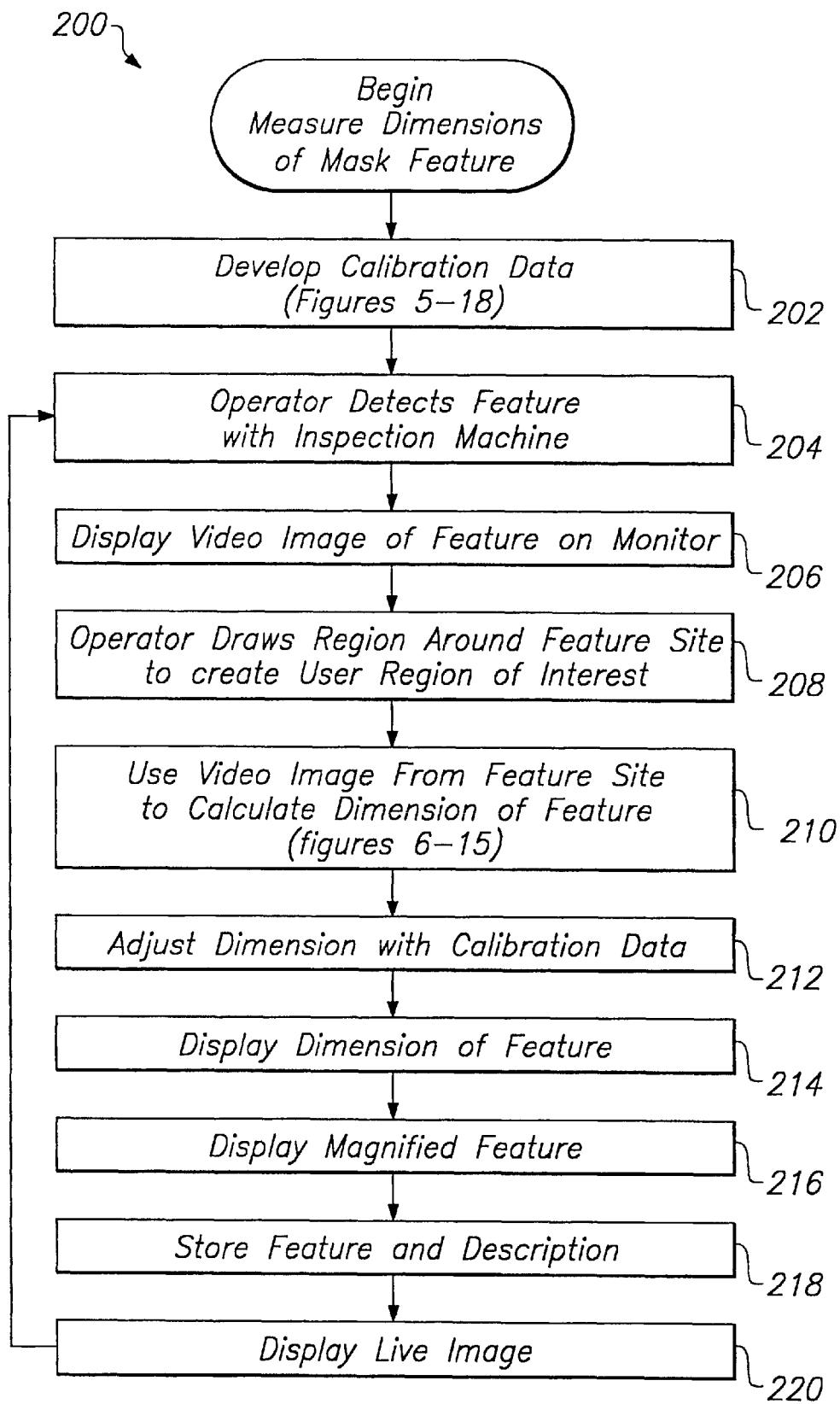
FIG. 4 is a flowchart for developing calibration data and measuring the dimensions of a feature of a photographic mask according to one embodiment.

Now having described examples of various of the types of defects and features that may be measured using the present invention, a technique 200 for measuring various dimensions of these features is shown in FIG. 4. In one embodiment of the invention, an operator uses the inspection machine of FIG. 1 to inspect a photomask and identify features. Once a feature is found, the operator is then able to measure in-place a dimension of the feature using a connected computer which receives live video information from the inspection machine. Thus, analysis and measurement of the feature occurs while the mask is in place in the inspection machine and there is no need to remove the mask to another machine for measurement of a feature. This technique allows for extremely rapid measurements to be made. Measurements may be made of features of known sizes for producing calibration data, or of features of unknown sizes in a production environment.

In step 202, calibration data is developed using features of known sizes (such as from a VERIMASK) on the inspection machine that will be used to measure the actual defects. The calibration data is used to correct for non-linearities in the relationship between measured sizes and actual sizes. The operator interacts with the inspection machine to develop the calibration data preferably using a sequence of steps similar to steps 204–208, although any other suitable technique may be used in order to develop the calibration data. This step will be explained in greater detail below with reference to FIGS. 5–15.

Once the calibration data has been obtained for any number of feature types, this data is stored in the calibration database 54 of FIG. 2 and may appear in graph form as shown in any of FIGS. 14–16. These graph figures will now be explained before returning to step 204 of FIG. 4.

FIGS. 14A–14D and FIGS. 15A–15D show calibration plots for each of specific types of defects, while FIGS. 16A–16D show calibration plots for specific types of lines. Each of the graphs has for a vertical axis a measured value for the diameter (or width) of the feature in pixels. Each horizontal axis is the true reference diameter (or width) of the feature in microns as determined from an AFM measurement, a Vickers measurement, or other standard. Both the AFM measurement and the Vickers measurement are performed on very expensive, slow microscopes that are not suitable for production purposes but are extremely accurate. An objective absolute standard for obtaining reference measurements would be an NIST version of a VERIMASK plate. Other dimensions could be represented in these calibration plots such as feature area, height, etc.

Figure 14A:
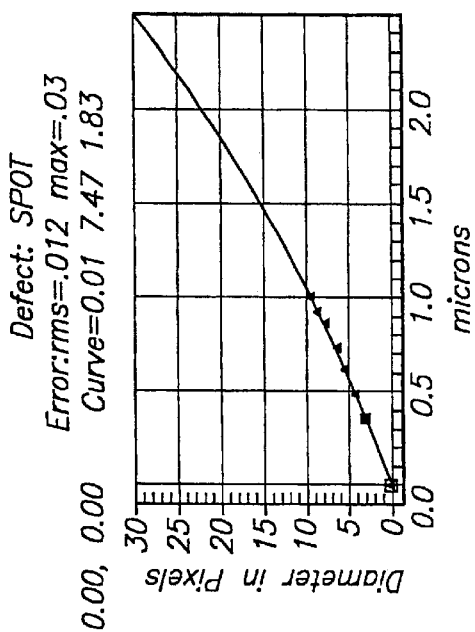
FIGS. 14A through 14D are calibration graphs for particular types of defects from which a reference measurement was obtained using an atomic force microscope (AFM).
Figure 14B:
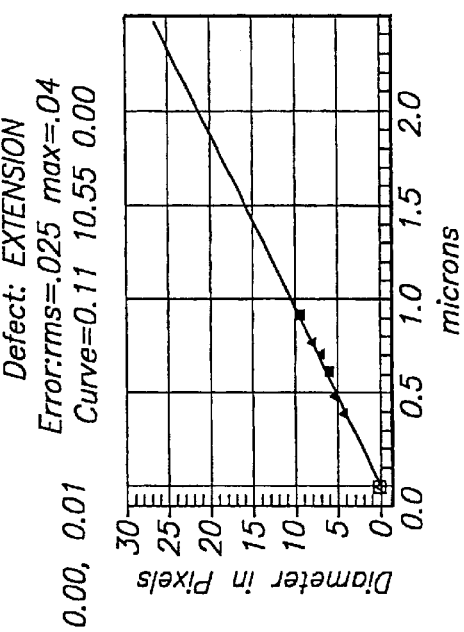
Figure 14C:
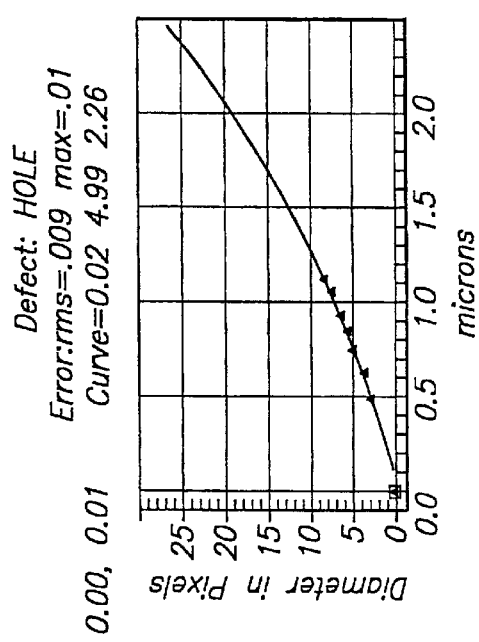
Figure 14D:
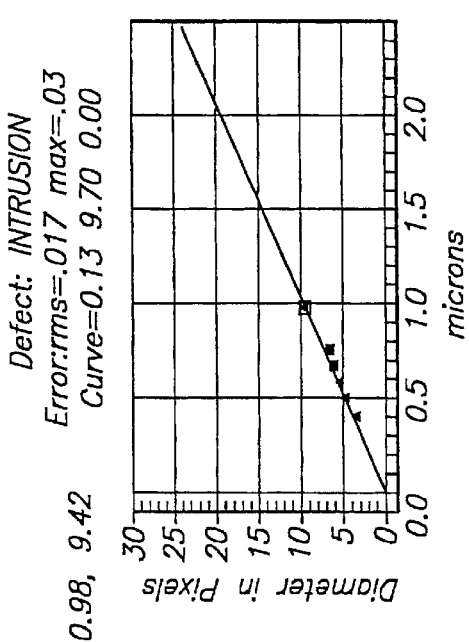
Figure 15A:
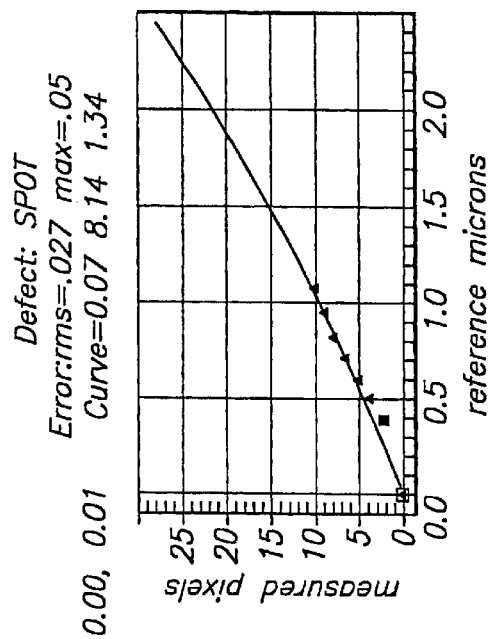
FIGS. 15A through 15D are calibration graphs for different types of defects from which a reference measurement was obtained using a Vickers machine.
Figure 15B:
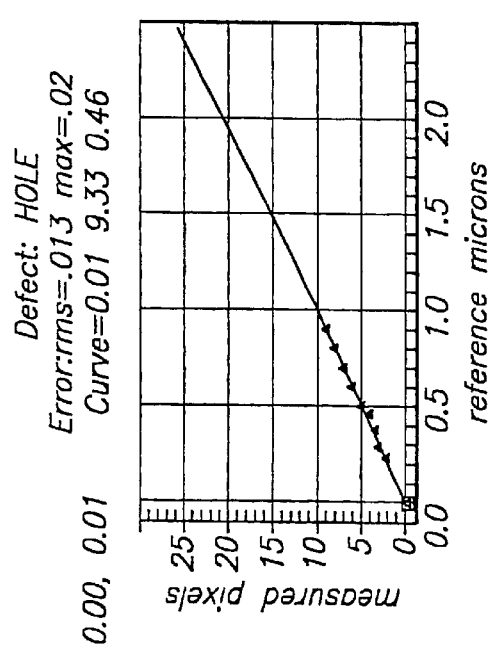
Figure 15C:
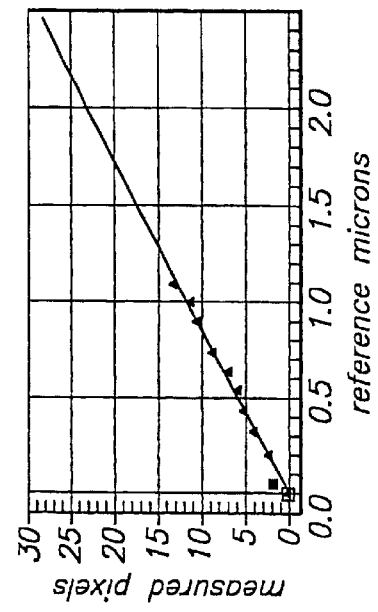
Figure 15D:
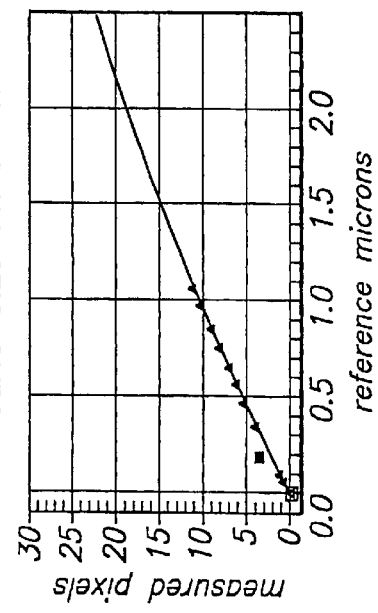
Figure 16A:
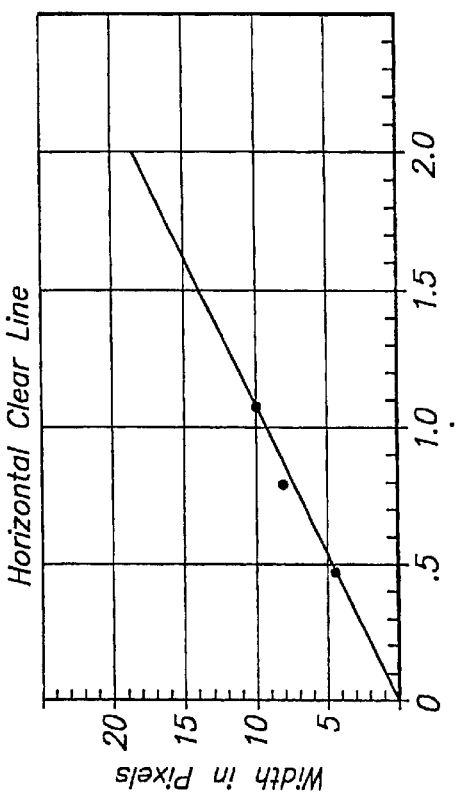
FIGS. 16A through 16D are example calibration graphs for different types of line widths as they may appear once a reference measurement is obtained.
Figure 16B:
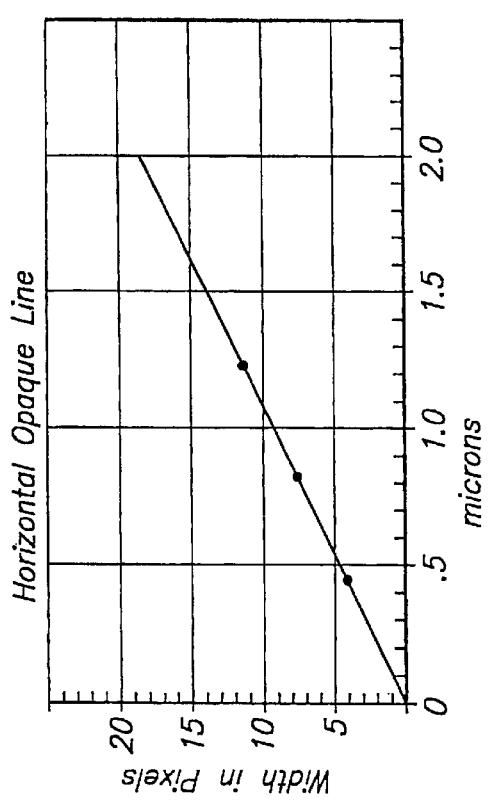
Figure 16C:
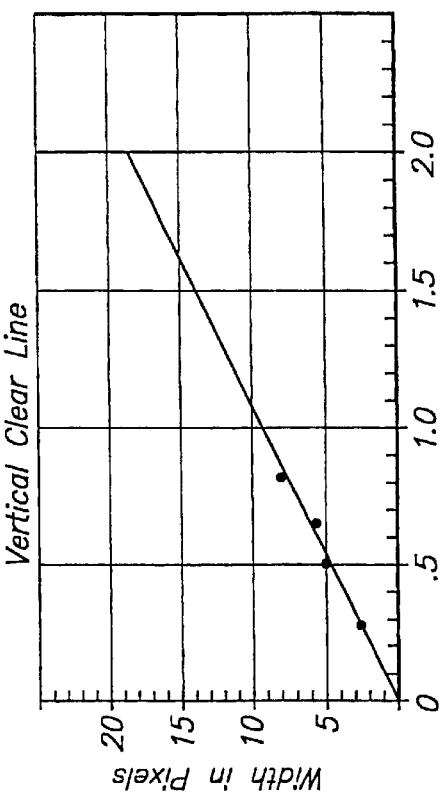
Figure 16D:
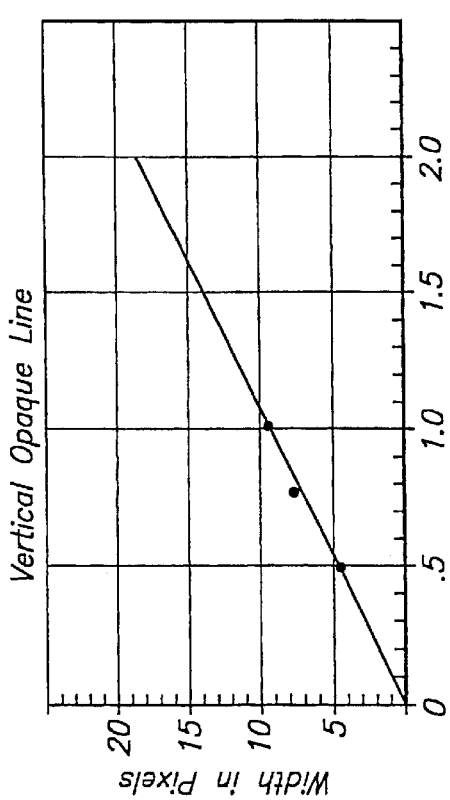

FIGS. 14A–14D and 15A–15D show respectively calibration curves for the defects hole, spot, intrusion and extension. FIGS. 14A–14B use a reference micron measurement from an AFM machine, while FIGS. 15A–15D use a reference micron measurement from a Vickers machine. FIGS. 16A–16D are possible calibration plots for line widths of horizontal opaque lines, horizontal clear lines, vertical opaque lines and vertical clear lines, respectively, and are illustrative of possible results for measuring line widths using any suitable reference measurement machine such as an AFM or Vickers.

For each feature type (hole, spot, etc.), the measurement tool is used to measure a number of features of different known sizes of that feature type using a known standard such as a VERIMASK in order to develop data points and a calibration curve such as those seen in FIGS. 14, 15 and 16. Because measurements of different features yield different results due to the inherent nature of the feature, having individual plots for each feature is advantageous in that more accurate measurements can be made for the actual features of that feature type. For example, referring to FIG. 14A, a measured hole defect having a diameter in pixels of twenty has a true size of 2.1 microns. And with reference to FIG. 14B, measurement of a spot defect having a diameter of twenty pixels results in a true size of 1.8 microns. Thus, it can be seen that for a measured value of twenty pixels for a defect, there is a difference of 0.3 microns in size depending upon whether the defect is a hole or a spot. Thus, development of calibration curves for each defect or line width is advantageous in that it results in greater accuracy for a measurement.

Additionally, separate calibration data for individual features can be developed for each objective of an inspection machine. Different objectives may have different characteristics affecting feature measurement. Also, the presence or absence of the compensation glass in an inspection machine (as required with through-the-pellicle KLA inspection) may cause different measurement results. Separate calibration data for individual features can also be developed for these situations. In general, a calibration plot can be developed for any unique combination of hardware in an inspection machine in order to compensate for its characteristics.

Dimension Measurement High Level Flow

Once calibration data has been developed for each type of feature (such as shown in the graphs of FIGS. 14, 15 and 16), the measurement tool is then ready to measure the dimensions of actual features. In step 204, the operator detects a feature such as a defect or line width using the inspection machine. In this step the inspection machine scans the mask and identifies a feature. The inspection machine may identify a feature automatically, or the operator may assist in the identification of the feature. This inspection of a photomask may occur in a mask shop before the mask is shipped out to a customer, or may also occur in a wafer fabrication shop when a mask is received. Once a feature is detected, the inspection machine enters review mode and in step 206 the video image of the feature site is displayed on the monitor of the computer.

Next, in step 208 the operator draws a region (or user region of interest) around the feature to be measured (such as shown in FIG. 3). A wide variety of techniques may be used by the operator to indicate a user region of interest around the feature. By way of example, the operator may use a mouse, track ball or other input device to drag a region around the feature. Advantageously, the operator is not required to exercise judgment in placing the region exactly around the feature, but is only required to roughly place a region around the general area of the feature to be measured. Thus, operator judgment does not effect the outcome of the measurement, because the measurement tool is adapted to automatically identify the type of feature within the feature site and measure its dimensions automatically and accurately without further operator intervention.

Once the feature has been surrounded with a user region of interest, in step 210 the video image from the feature site is used to calculate the desired dimension of the feature. Dimensions of the feature to be calculated may include its area, diameter, width, height, and other dimensions. In one preferred embodiment, the calculation of a dimension of an actual feature may take place in the same way as test features of known sizes are measured in step 202 in developing the calibration data. This calculation of a dimension of an actual feature may take place as described in FIGS. 6–13.

Once a dimension of a feature has been calculated, the dimension (such as the diameter) of a feature is adjusted in step 212 using the calibration data contained in the calibration database (and as shown in graph form in the examples of FIGS. 14–16). For example, referring now to FIG. 14A, if the diameter of a hole defect has been measured to be five pixels, then referring to the plot reveals that a diameter of five pixels is 0.7 microns in width. In this fashion, a measured dimension of a feature in pixels can be referenced to the calibration data in order to obtain an extremely accurate "true" value for the dimension of the feature in microns. This technique can be used for any dimensions such as area, diameter, width, height, etc. The creation of this calibration database which is represented graphically in the example plots of FIGS. 14, 15 and 16 will be explained in greater detail below with reference to FIG. 5.

Once the dimension (such as diameter, width, height, etc.) of the feature has been accurately determined, in step 214 the dimension of the feature in microns is displayed on the computer monitor. In step 216 the feature image is magnified and displayed with a one by one micron grid for a sanity check. In step 218, the operator has the option to store the feature and its measured dimensions along with a description into a feature database for later retrieval and analysis. The operator may also print images of the feature and its dimensions at this time. It should be noted that at any time in this process, previously stored features and dimensions may be reviewed, and these selected features and associated text can be selected and printed. Once the operator has finished with a particular feature, in step 220 the live image display is returned to the computer monitor and the operator continues to detect and measure additional features in step 204.

Development of Calibration Data

Figure 5:
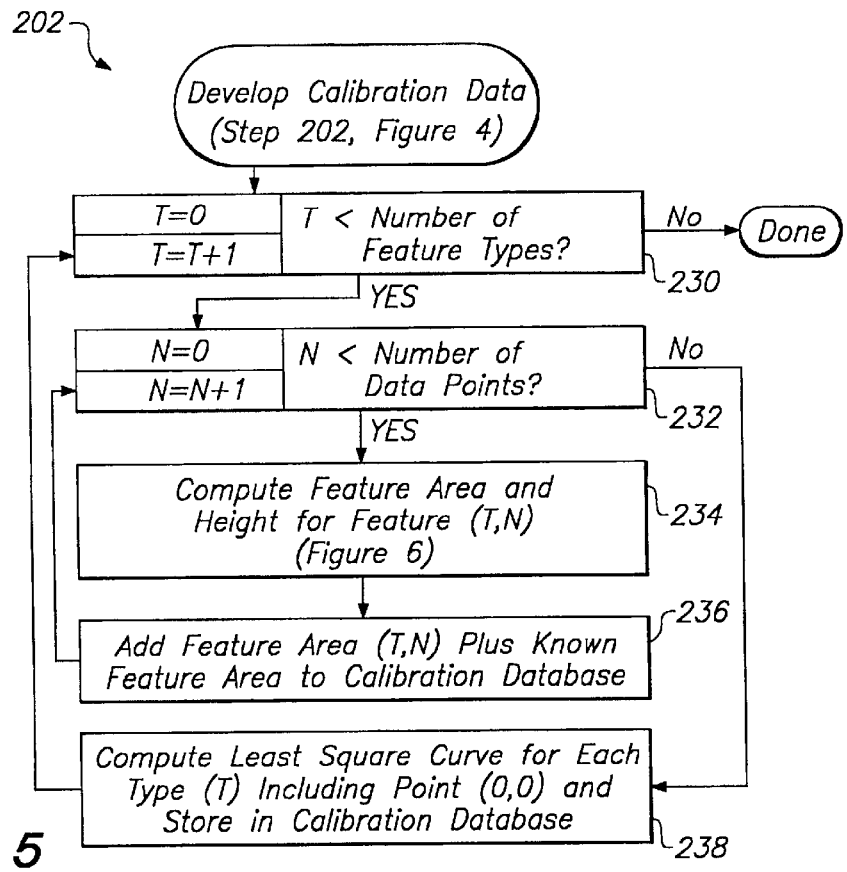
FIG. 5 is a flowchart for the develop calibration data step of FIG. 4.

FIG. 5 illustrates one embodiment of a technique for performing the develop calibration data step 202 of FIG. 4. This step is used to develop calibration data for each of a variety of feature types such as defects and lines. For each type of defect and/or lines, a number of different sizes for that particular defect or line width will be measured in order to produce a number of data points for producing a polynomial curve. A polynomial curve typically results from the plotting of data points for features less than 1 micron in size because these sizes are approaching the size of the light photons used to measure the feature. In other words, the relationship is non-linear and a polynomial curve results (often quadratic) because the features are so small that the size of the light photons (about 0.5 microns) used to measure the features starts to interfere with the measurement. A polynomial curve is advantageous when the size of features to be measured is less than twice the wavelength of the light used to illuminate and measure the feature. By way of example, for visible light, a polynomial curve is advantageous for features less than one micron in diameter.

For example, referring to the hole defect plot of FIG. 14A, it can be seen that seven different sizes of hole defects ranging from about 0.5 microns to 1.1 microns have been measured in order to develop a non-linear calibration curve for that type of defect. Thus, a measured value for an actual hole defect may reference this data to obtain a more accurate measurement.

Step 230 implements a loop through each type of feature and develops calibration data to produce a calibration plot for each feature type. In one embodiment, there are eight feature types that include the defects hole, spot, intrusion and extension, and line width features that include horizontal opaque lines, horizontal clear lines, vertical opaque lines, and vertical clear lines. Of course, calibration plots may be developed for other feature types. When all features have been analyzed and measured this step is done. Step 232 implements a loop that measures a variety of data points for each type of feature. For example, as shown in the hole defect plot of FIG. 14A, there are seven sizes of holes that are measured that produce seven data points for the plot resulting in a particular calibration curve for that type of defect. Any number of sizes of a feature type may be measured in this step. For each size of these artificial features, steps 234 and 236 are executed. Once each of the sizes has been measured, control moves to step 238.

In step 234 the feature area and height for a particular size of a particular feature type is computed. This step will be explained in greater detail below with reference to FIG. 6. Also, the line width may be calculated from the feature area because as seen in FIG. 10E, area 395 from profile 396 of line 392 when divided by the region of interest (ROI) height yields line width 394. Additionally, this step may also be used to calculate dimensions of an actual feature to be measured such as described in step 210 of FIG. 4.

In step 236 the computed feature area for the particular size of a particular feature is added to the calibration database along with the previously (or known) feature size. In this step, the measured height of the feature may also be added to the calibration database.

The calibration database may be implemented and organized in a wide variety of manners. By way of example, the calibration database contains a list of the measured feature area (or other dimension) for each defect size and its corresponding reference size in microns. The reference size in microns is known because the VERIMASK has artificially produced defects and line widths with known sizes that have been measured using an extremely accurate measurement device such as an atomic force microscope (AFM) or a Vickers machine. In step 236 when the measured feature area is added to the calibration database, the operator may be prompted to enter the reference size in microns, or the reference size in microns may be entered automatically along with the measured size in pixels by the computer. In one embodiment, a defect is assumed to be circular, the diameter of the defect is determined from the measured feature area and this diameter in pixels is entered into the calibration database along with its corresponding true diameter in reference microns. Such an entry in the calibration database represents one of the data points such as those shown in FIG. 14A or any of the other plots shown in FIGS. 14, 15 or 16. Once step 232 adds the data associated with one feature size, control returns to step 232.

Once step 232 has finished computing all of the data points for a particular feature type, control moves to step 238. In step 238, the data points developed for a particular feature type are used to produce a calibration curve such as those seen in FIGS. 14, 15 and 16. This calibration curve and its corresponding polynomial formula are then also stored within the calibration database for later reference in determining the actual size of an actual defect. In one embodiment of the invention, step 238 is performed by computing a least square curve for each feature type (including the data point 0.0). This curve and its corresponding polynomial formula (such as $ax^2+bx+c$) then stored in the calibration database. Once a calibration curve has been computed and stored in the calibration database for a particular type of feature, control returns to step 230 and calibration curves are developed for each of the remaining types of features. Once all of the calibration data has been obtained for each feature type, then the develop calibration data step is done.

Profile Development, Flux, Area and Line Measurement

Figure 6:
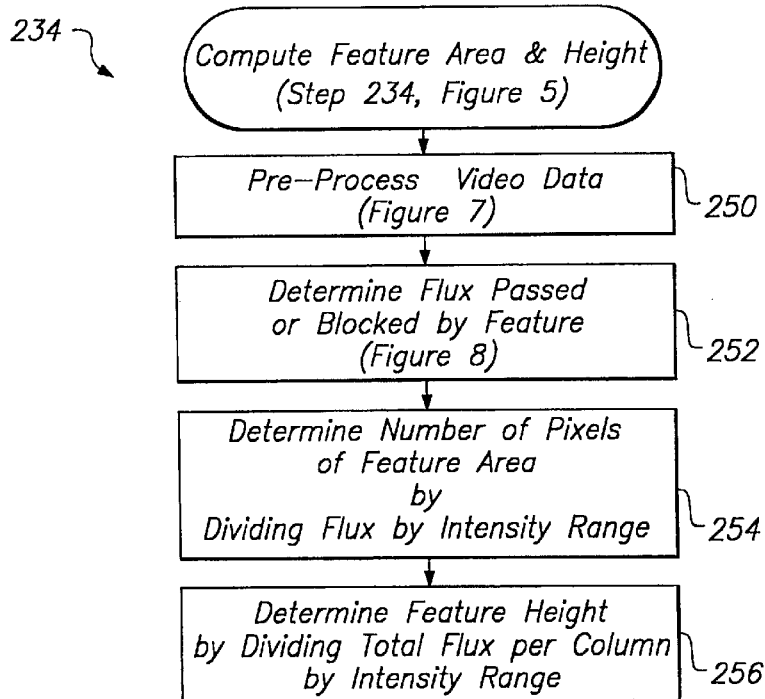
FIG. 6 is a flowchart for the compute feature area step of FIG. 5.

FIG. 6 illustrates one embodiment of a technique for computing the feature area and height, step 234 of FIG. 5.

In step 250, the video data is pre-processed in order to determine an intensity range, determine the feature type, determine a size for system regions of interest around the feature and to produce a good quality flux source image from which the flux passing through the feature will be determined. The video data being processed may represent test data for a standard feature of a known size used for developing calibration data, or may represent video data of an actual feature to be measured. This step will be explained in greater detail below with reference to FIG. 7.

Once the video data has been pre-processed and a good quality flux source image produced, in step 252 the flux that is passed or blocked by the feature is determined. This step develops multiple profiles of a particular feature and chooses the best profile in order to determine the flux. Flux corresponds to the number of light photons passing through a medium and is expressed in units of scaled photons. An opaque feature such as a spot or a line blocks the passage of photons and reduces flux, while a clear portion of a mask such as formed by the space between lines, or the gap created by an intrusion into a line, passes photons easily and results in an increase in flux. This step will be explained in greater detail below with reference to FIG. 8.

Once the flux has been determined, in step 254 the number of pixels of the feature area is determined by dividing the determined flux by the intensity range. In this fashion, the feature area in pixels can be determined and the diameter of the defect or the width of the line can be easily determined from the feature area. For example, the line width dimension may be calculated from the feature area because as seen in FIG. 10E, area 395 from profile 396 of line 392 when divided by the region of interest (ROI) height yields line width 394. Because flux is measured in photons, and the intensity range is measured in photons/square pixel, the division of flux by intensity range gives an area in square pixels which yields a diameter or width. This measured diameter or width in pixels can then be added to the calibration database along with the reference feature dimension (if calibration data is being developed), or the diameter or width in pixels can be referenced to one of the calibration plots in order to return a true size in microns (if an actual defect or line width is being measured).

In step 256 the total flux determined from one column of the intensity profile can be used to determine the height of a defect or line by dividing the total flux by the intensity range. This height in pixels can then be added to the calibration database (for test features) or may be referenced to a calibration plot for determining an accurate height of actual features. Determining height is advantageous for evaluating how far edge defects extend from, or intrude into a line.

Figure 7:
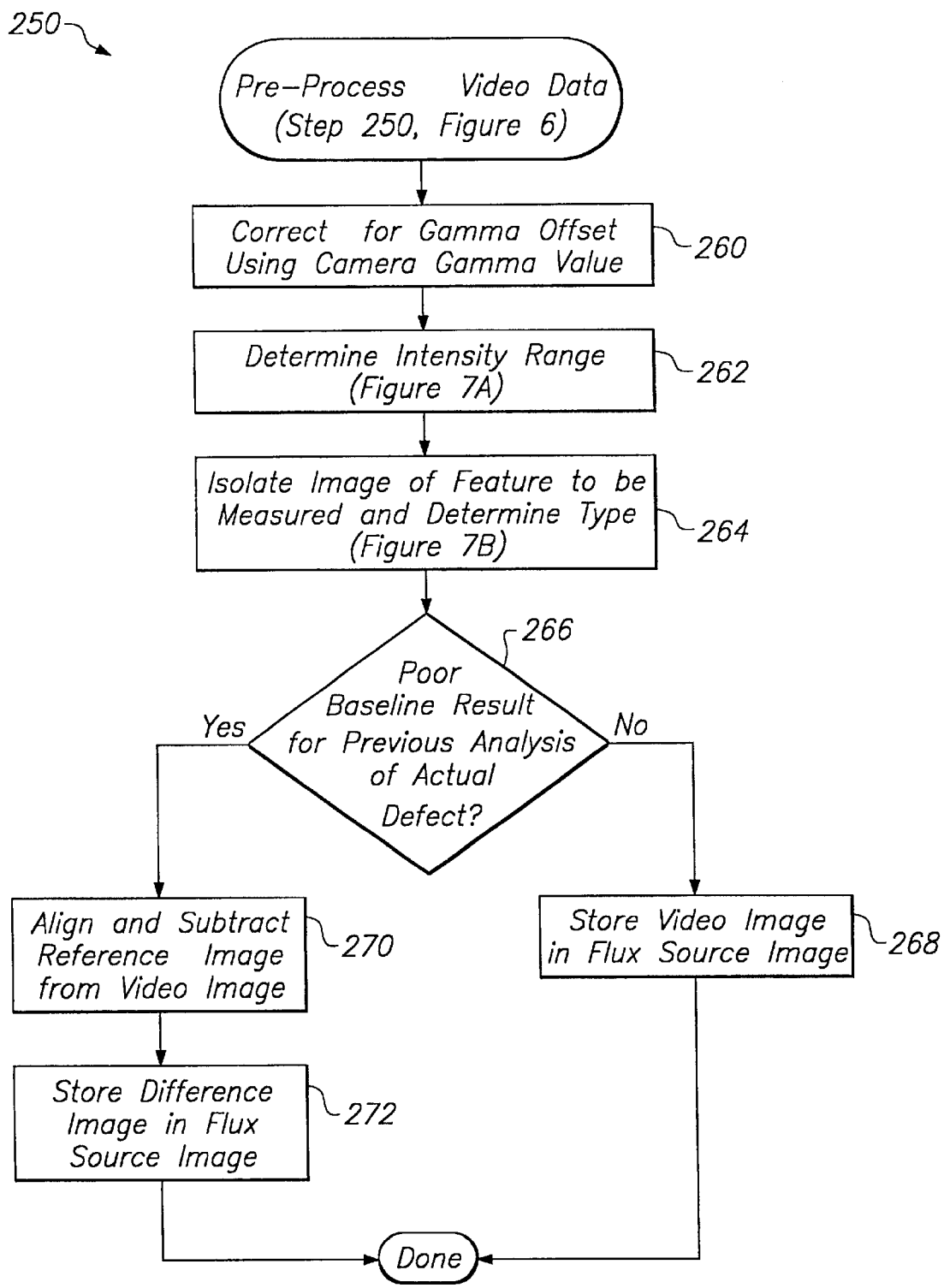
FIG. 7 is a flowchart for the pre-process video data step of FIG. 6.

FIG. 7 illustrates an embodiment of the pre-process video data step of FIG. 6. This step is used to determine the intensity range for the feature, determine the type of the feature, to obtain a reference image if needed, and to produce a good quality flux source image. In step 260 the camera gamma value is used to correct for the gamma offset of the camera optics. A camera gamma value is intrinsic to all camera electronics and has a known value for each camera. Because the light input to the camera versus the voltage output is non-linear, it is corrected for in this step.

In step 262 the intensity range for the feature to be measured is determined. An intensity value or range may be determined in a wide variety of manners. By way of example, step 262 presents one possible technique. The value for intensity range represents a range from the dark peak mean to the bright peak mean and is constant for changes in illumination or camera gain. Intensity range is expressed in digitized units (representing photons/square pixel), ranging typically from 0 to 255 for a gray scale image. A "0" value represents one end of the spectrum such as chrome being present, and a "255" value represents the other end such as a clear portion of the mask. Generally, a value of 255 for intensity is equivalent to about 10,000 photons. This step will be explained in greater detail below with reference to FIG. 7A.

In step 264 the feature to be measured is isolated and its type is determined. A bounding box is used to surround the feature and to determine its type. This step will be explained in greater detail below with reference to FIG. 7B.

Figure 13:
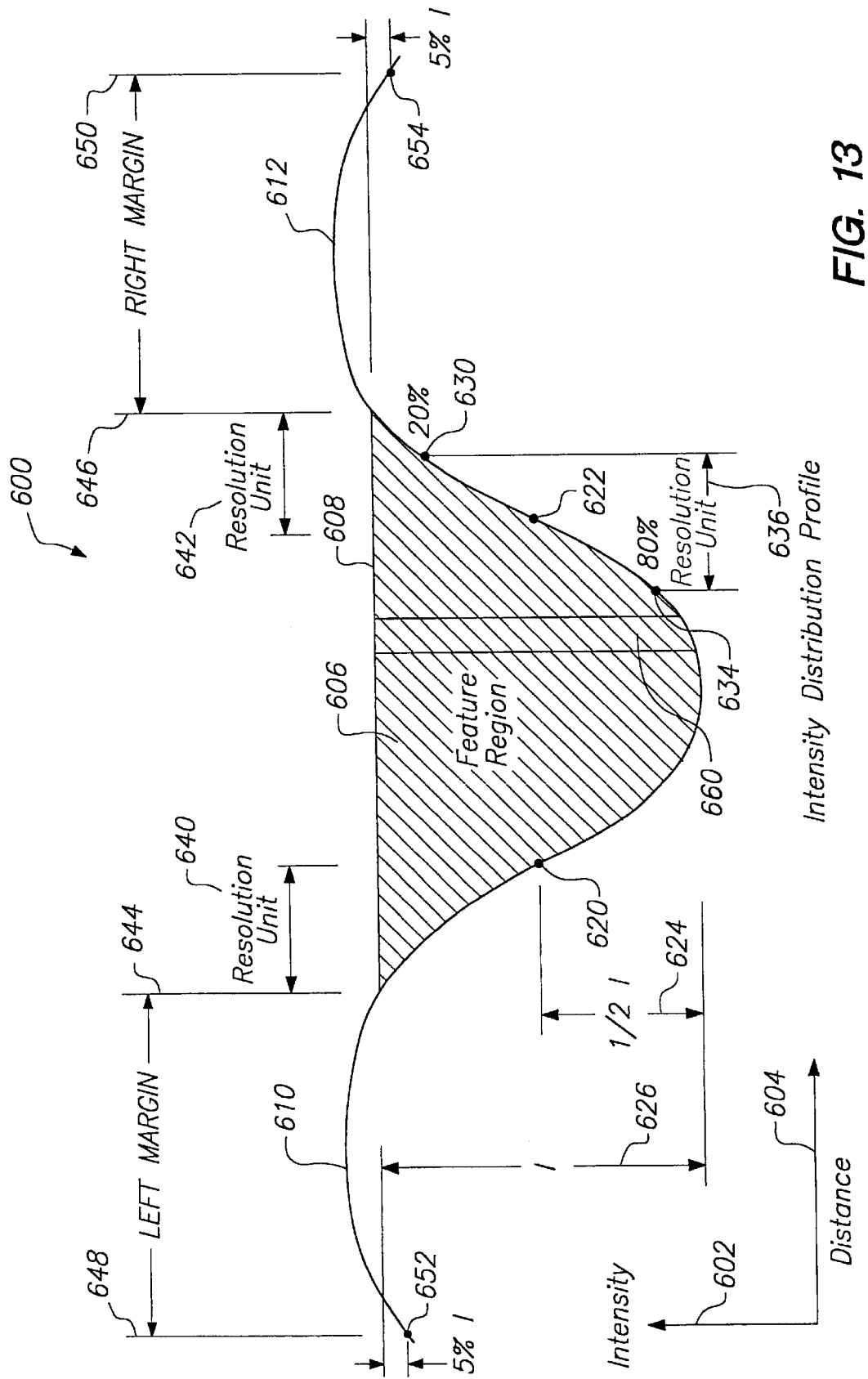
FIG. 13 illustrates in greater detail the intensity distribution profile of FIG. 11A.

The following steps 266–272 ensure that a good quality flux source image is available for producing a good profile. The development and use of profiles in determining flux will be explained in greater detail below with reference to FIG. 8. Actual features to be measured often end up producing a low quality profile having a poor baseline (jagged, uneven, or non-linear) because the feature may be fairly complex. For example, a defect such as an edge defect may be located on a curve of a line rather than on a straight edge, and isolated defects may be located extremely close to other features which effect the developed profile for that feature. Thus, for actual features measured, if a good profile can not be obtained, it may be necessary to obtain a reference image for that feature. FIG. 13 is an example of a profile having a good baseline, i.e., the baseline is fairly linear and the standard deviations of its left and right margins are fairly low.

If a profile has been developed for an actual feature (as will be discussed in FIG. 8), and that profile has a baseline that is not straight, then steps 270 and 272 are performed in order to obtain a good quality flux source image. In step 270 the operator is prompted to obtain the reference image for the feature site under consideration and this reference image is then subtracted from the current actual feature site which contains the defect. A reference image is a good image of the mask as it should appear without a defect. This reference image may be obtained from a mask database, or from a mask on a previous die. By subtracting the reference image from the actual image, any complex features surrounding the feature to be measured are removed from the image and only the defect to be measured remains in the image. Next, in step 272 this difference image is stored as the flux source image.

On the other hand, artificial defects and most of the actual features are treated differently. Because a standard, artificial defect used for calibration purposes is very simple and not complex, such a feature usually always has a good profile with a straight baseline. Thus, for calibration features, the result of step 266 is no, and in step 268 the current video image is stored as the flux source image. Also, for the measurement of actual features, the first time the feature is measured there is no profile developed at this point in time so the video image for that feature will also be stored as the flux source image in step 268. Additionally, for measurement of line widths, a good profile is usually obtained so step 268 is performed. Once a video image has been stored as the flux source image (in either steps 268 or 272), the measurement tool is ready to determine the flux passed or blocked by the feature by referring to the flux source image.

Figure 7A:
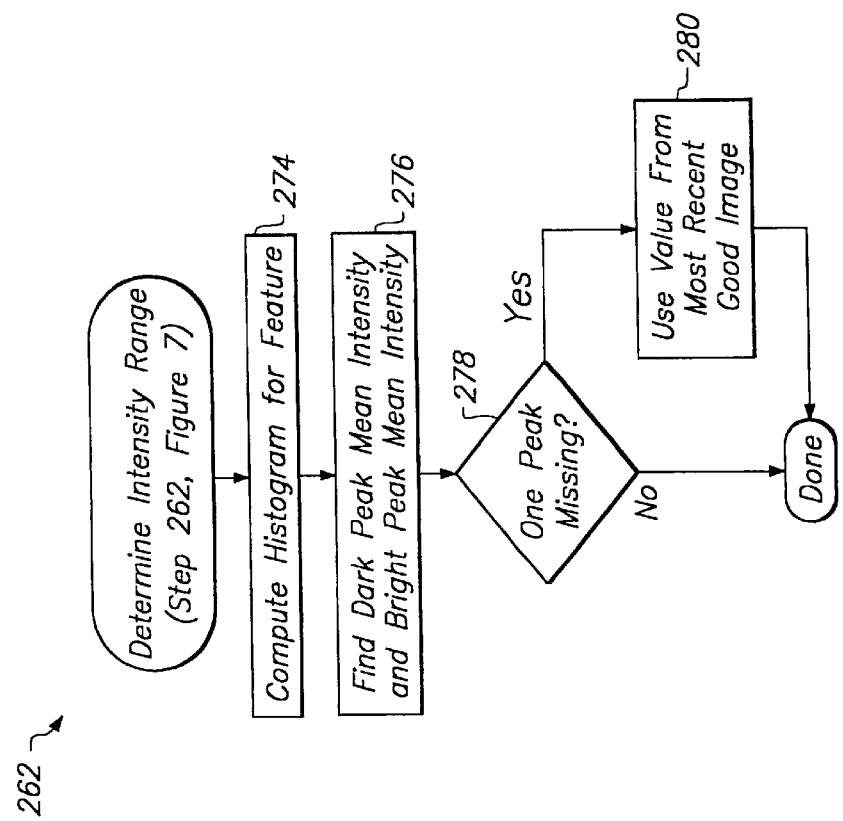
FIG. 7A is a flowchart for the determine intensity range step of FIG. 7.

FIG. 7A illustrates one technique for determining the intensity range, step 262 of FIG. 7. The intensity range is used along with the flux determined in order to determine the number of pixels in the feature area. A value for the intensity range is used instead of just an intensity value to compensate for light changes affecting the flux value. For example, if the camera gain doubles or more illumination is used on a feature then the flux would double and affect the measurement of the feature dimension. But if the illumination doubles, the intensity range would also double and a measurement would stay constant.

In step 274 an intensity histogram for the feature is computed. A histogram is a plot of light intensity values versus areas occupied by each intensity value and is used in order to determine the intensity range for the feature site. FIG. 9 illustrates an example of a histogram 300 that may be used to determine the intensity range of a particular feature. This histogram example has an intensity axis 302 ranging from 0 to 255 and an area axis 304 representing the area in pixels that a particular intensity occupies. This example feature has a histogram 306 defining dark intensity areas 308, bright intensity areas 310, and intermediate gray intensity areas 312. The top of the dark area yields a dark peak mean 314 and the top of the bright area yields a bright peak mean at 316. Using the computed histogram for this feature, in step 276 the dark peak mean intensity and the bright peak mean intensity are determined by reference to the dark peak mean 314 and the bright peak mean 316 of the computed histogram. The intensity range is then determined by subtracting the dark peak mean intensity from the bright peak mean intensity. Thus, were illumination to double, the peaks would be twice as far apart and the intensity range would also double and a measured feature area would remain constant.

Step 278 determines whether a good histogram has been obtained by determining whether one of the peaks is missing. A good histogram will typically have a dark peak that is four times greater in area than the valley of the gray region 312 and a bright peak that is four times greater in area than the valley region. If a good histogram cannot be obtained by analyzing a small region around the defect, then a larger region around the defect is analyzed. For isolated defects, such as spots or holes, there will either be all black or all white around the defect, so it makes no difference how big the analyzed image is. If a good histogram cannot be obtained by analyzing a larger region around the defect, then in step 280 the histogram value from the best recent good image is used.

Figure 7B:
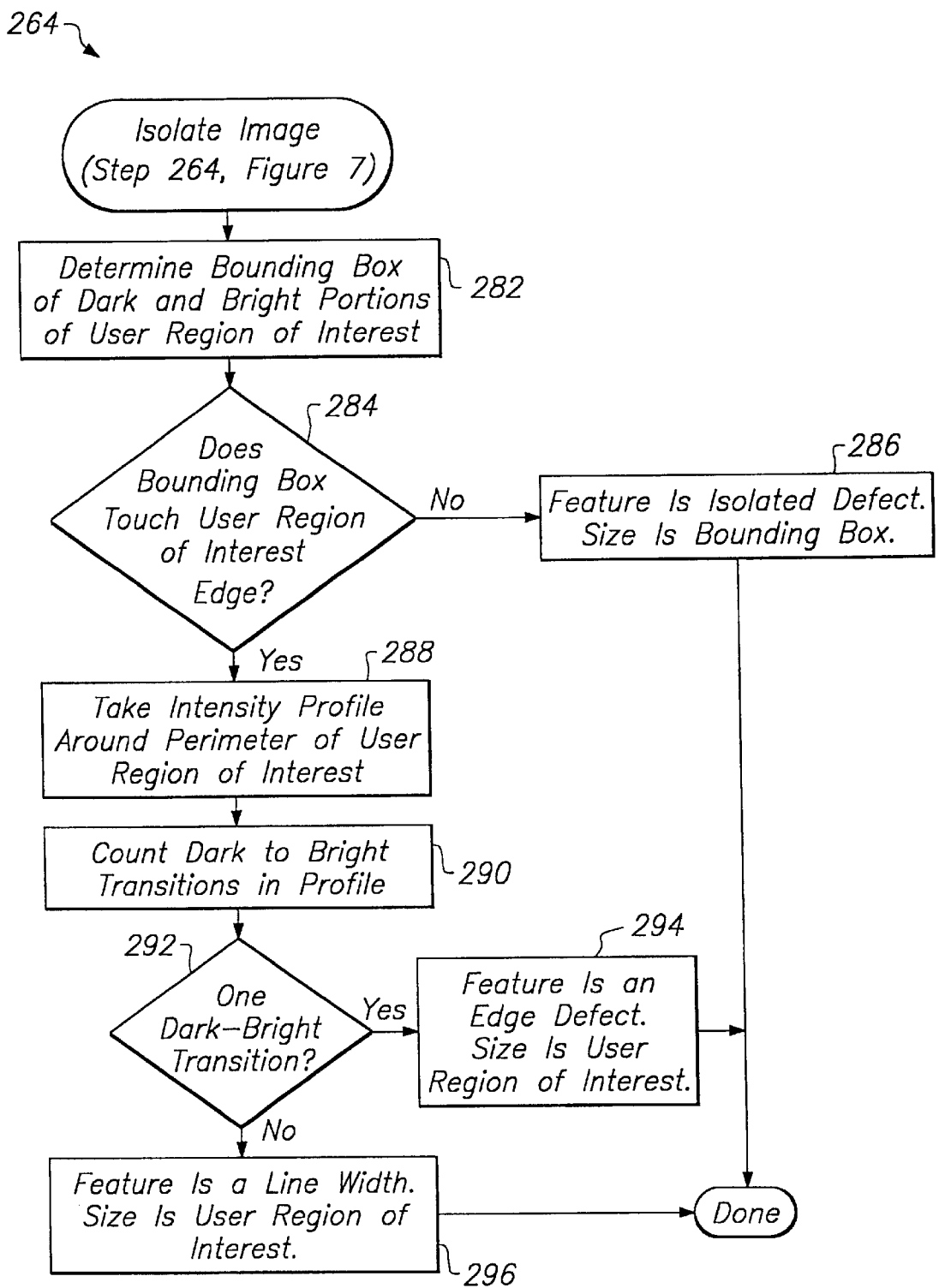
FIG. 7B is a flowchart for the isolate image and determine feature step of FIG. 7.

FIG. 7B illustrates a technique for isolating the image of the feature to be measured and for determining its type, step 264 of FIG. 7. This step returns a size for the system regions of interest used in developing profiles of FIG. 8 and also determines the type of the feature. In step 282, bounding boxes are determined for the dark and bright portions within the video image of the user region of interest. A bounding box determines the extent of contiguous dark or bright features. Determining bounding boxes may be done in a wide variety of manners. By way of example, the technique known as "blob analysis" may be used to determine the bounding boxes.

For example, feature site 70 of FIG. 3A shows a spot defect 71 surrounded by a bounding box 73. This bounding box 73 tightly conforms to the outline of spot 71 and is completely contained within user region of interest 72. A bounding box for hole 76 of FIG. 3B would similarly tightly surround the hole and would be contained completely within the user region of interest. By contrast, bounding boxes formed for other features such as the extension, intrusion and line of FIGS. 3C, 3D and 3E would not be completely contained with the user region of interest but would be collinear with the identified user region of interest. Bounding boxes for these features touch the user region of interest because the dark and bright areas of the feature are not completely isolated within the user region of interest but extend to the border of the user region of interest.

In this way, an analysis of the bounding boxes formed can help determine the type of the feature. In step 284 it is determined if the bounding box for a dark or bright feature touches the edge of the user region of interest. If the answer is no, then in step 286 it is determined that the feature is an isolated defect such as a spot or a hole, and the size used to help determine the size of system regions of interest is determined to be the size of the bounding box.

However, if the bounding box does touch the user region of interest, then the feature may be an edge defect or a line width. Thus, in step 288 an intensity profile is taken around the perimeter of the user region of interest. Because the user region of interest may be asymmetrical, it is advantageous to take the profile around the perimeter, although in an ideal situation a portion of the perimeter may be used. This intensity profile will identify dark and bright areas and transitions in-between. In step 290 the number of dark to bright (or bright to dark) transitions in the intensity profile are counted. An example of the use of counting such dark to bright transitions may be seen in the examples of FIGS. 3D and 3E. For example, in FIG. 3D the edge defect within the user region of interest has only one bright area outside the line and the one dark area being the line itself. Therefore, there is only one dark to bright transition from the line to the area outside the line. By contrast, FIG. 3E shows how bright regions 95 and 96 are outside of the dark line region 91. Thus, there are two dark to bright transitions, one on each side of line 91.

The number of dark to bright transitions may then be used to determine the type of feature. Step 292 tests whether there is one dark to bright transition. If so, then in step 294 it is determined that the feature is an edge defect and the size used to help determine the size of system regions of interest is determined to be the complete user region of interest. However, if there is more than one dark to bright transition, then step 296 determines that the feature is not a defect but is a line width, and the size used to help determine the size of system regions of interest is determined to be the user region of interest. After steps 286, 294 and 296 have completed, step 264 of FIG. 7 is done.

Figure 8:
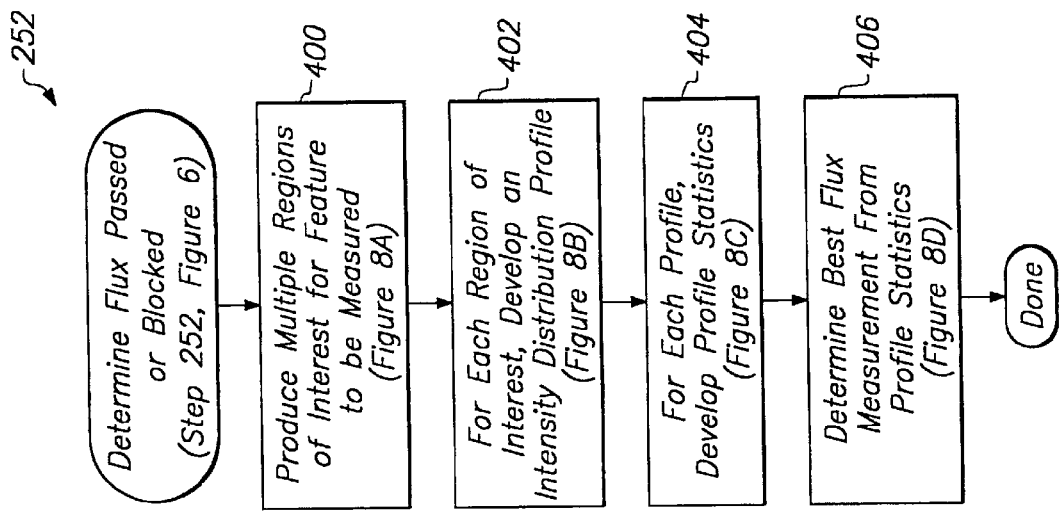
FIG. 8 is a flowchart for the determine flux step of FIG. 6.

Once the pre-processing of the video data has determined the intensity range for the feature, has determined the type of the feature and has returned a size for system regions of interest, FIG. 8 provides a technique by which the flux that is passed or blocked by the feature in the video image is determined, step 252 of FIG. 6. Once the flux is determined, then the area of the feature may be calculated. FIG. 8 illustrates a technique by which multiple regions of interest (system regions, as opposed to the original user region of interest) are each used to create a profile for the feature to be measured. These profiles are then analyzed to determine which profile provides the best flux measurement for the feature to be measured. Through the use of this technique, edge defects that lie along an edge angled off of the horizontal may be measured accurately, as well as line widths for lines that are not horizontal.

In step 400 multiple system regions of interest for a particular feature to be measured are produced depending upon whether the feature is a defect or a line width. These multiple regions of interest are additional regions of interest developed by the measurement tool and are distinct from the original user region of interest that the operator specifies in identifying a feature. This step will be discussed in greater detail below with reference to FIG. 8A. Next, in step 402 a profile is developed for each of the regions of interest produced in step 400 and is discussed in greater detail below with reference to FIG. 8B. In step 404 profile statistics are developed for each profile in order to determine which profile provides the best flux measurement and is discussed in greater detail below with reference to FIG. 8C. In step 406 the profile statistics for each of the profiles is used to determine which profile provides the best flux measurement for the feature of interest, and is discussed in greater detail below with reference to FIG. 8D. The best flux measurement is then used as the determined flux value for step 252 of FIG. 6.

Figure 8A:
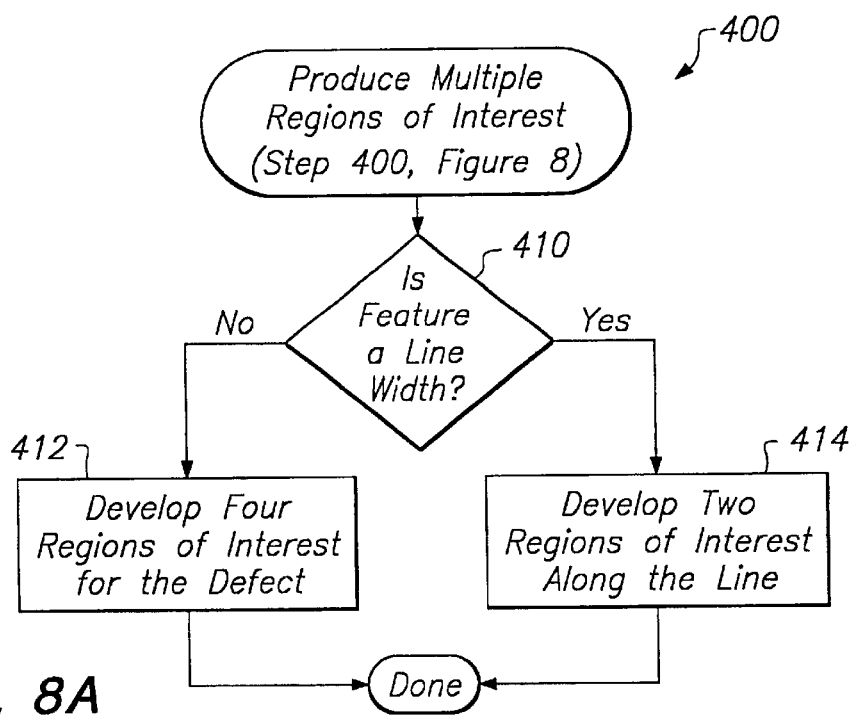
FIG. 8A is a flowchart for the produce multiple regions step of FIG. 8.

FIG. 8A illustrates one embodiment of a technique for producing multiple regions of interest, step 400 of FIG. 8. Step 410 tests whether the feature is a line width or a defect, the type of feature already having been determined above in FIG. 7B. If the feature is an isolated or edge defect, then in step 412 four system regions of interest are developed for the defect.

Examples of four possible system regions of interest developed for a spot defect (for example) are shown in FIGS. 10A–10D. FIG. 10A shows a vertical region of interest 350 surrounding a spot defect 352. FIG. 10B shows a horizontal region of interest 360 surrounding a spot defect 362, and FIGS. 10C and 10D show angled regions of interest 370 and 380 surrounding the spot defects 372 and 382 respectively. Of course, many other orientations for the multiple regions are possible.

Multiple regions of interest are useful for producing a good profile of the defect. If the defect is on an edge, then a profile is best taken parallel to the edge in order to obtain a good profile with a straight baseline. Also, if the defect is near or on a diagonal line, then the profile should be taken on the diagonal that is parallel to the diagonal line. And because these edges or lines may be horizontal, vertical, or at a 45 degree angle, multiple regions of interest that run parallel to these edges are useful. Most lines and edges on a photomask are horizontal or vertical, but some are at a 45 degree angle.

Because of feature crowding on a photomask (due to the ever decreasing size of the mask and its features), isolated defects may also often be found on or near a horizontal, vertical or diagonal line. Also, it is likely that a defect may be found on an edge. Thus, the development of multiple regions of interest ensure that at least one of the multiple regions of interest will enable a profile to be taken parallel to an edge near the defect.

Height 391 and width 393 conventions for system regions of interest are shown in FIG. 10E. The size and angle of each of the system regions of interest developed in step 412 for a defect may be determined in a wide variety of manners. By way of example, the width may be determined by multiplying the Blur Size by four, and the height may be determined by adding the Blur Size to a user defined height or to the size determined in FIG. 7B. The user defined height can be pre-programmed or chosen by the user from the computer. The angle for the regions of interest in FIGS. 10C and 10D may be any angle; a 45 degree angle works well.

The Blur Size is an empirically determined value in pixels that is an estimate of the resolution unit for the optics used; calculation of its value will be explained in greater detail below with reference to FIG. 13. It should be appreciated that any number of regions of interest may be developed, although developing fewer regions of interest may result in a poor profile being developed, leading to an inadequate measurement of the feature area. Once these multiple regions of interest have been developed in step 412, then step 400 is done.

Returning now to step 410, if the feature is determined to be a line width, then in step 414 two regions of interest are developed along the line to be measured. Examples of two regions of interest 396 and 398 are shown in FIG. 10E. These two regions of interest are developed along line 392 having a width 394. Two regions of interest are used to help determine the flux through a line because the line may be slightly angled. By providing two parallel regions of interest 396 and 398, the angle of the line can be corrected for as will be explained in greater detail below with reference to FIG. 8D. The height 391 and width 393 of these two regions of interest may be any suitable value. By way of example, a width equal to a user defined height (or the size determined in FIG. 7B) plus twice the Blur Size works well. A height equal to seven pixels also works well. Once these two regions have been developed in step 414 then step 400 is done.

Figure 8B:
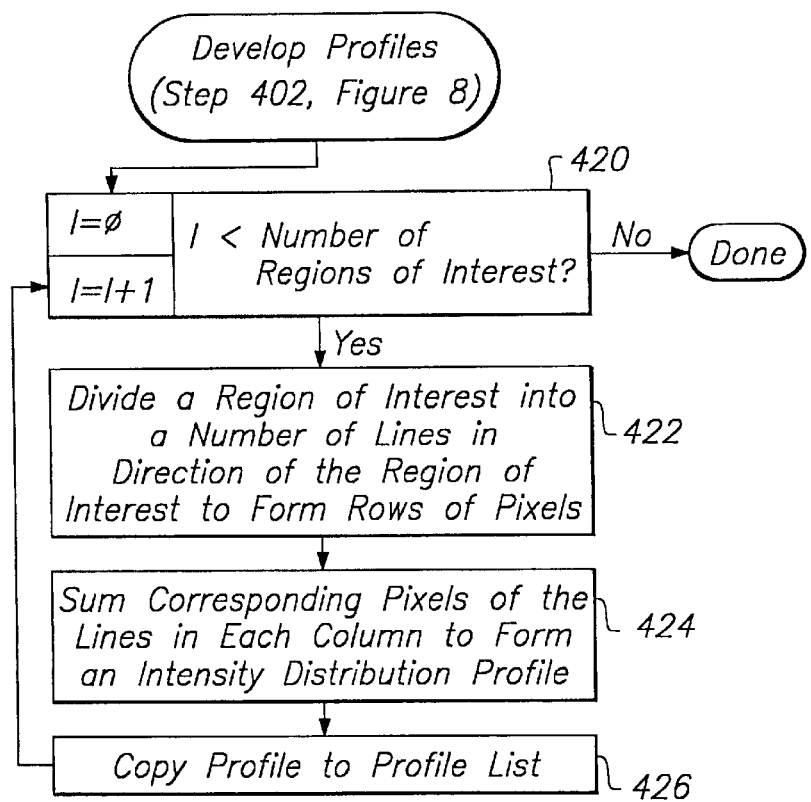
FIG. 8B is a flowchart for the develop profiles step of FIG. 8.

After the multiple regions of interest are produced, then in FIG. 8B a technique is shown for developing an intensity distribution profile for each of the produced system regions of interest. This technique will be explained with reference to FIGS. 11 and 12. Step 420 of FIG. 8B loops through steps 422–426 for each of the multiple regions of interest produced in step 400 of FIG. 8. Once a profile has been developed for each region of interest then step 402 is done.

In step 422 one of the multiple regions of interest is divided into a number of lines in the direction of the region of interest in order to form rows of pixels. This step is illustrated in FIG. 11A, for example. FIG. 11A shows a process 500 in which a region of interest 502 surrounding a spot defect 504 is used to develop a profile 506. Because region of interest 502 derives from a video image of the feature site, it is composed of pixels. This step divides the region of interest into rows of pixels 508 along the direction of the region of interest, which in this case happens to be horizontal. A region of interest that was angled would be divided into rows of pixels that are parallel to its length.

Next, in step 424 corresponding pixels in the rows of pixels 508 are summed in each column in order to form an intensity distribution profile 506. As shown in FIG. 11A, a column of pixels 510 is summed in order to form a portion of the profile 506. Using this technique, profile 506 has a flat baseline 512 except in the location of the spot defect 504 which is where a dip in the intensity of the profile 514 is caused by spot defect 504. The intensity dips at this point because spot defect 504 prevents flux from passing through the spot.

Examples of developed profiles for other types of defects are shown in FIGS. 11B and 11C. FIG. 11B shows a process 510 in which a region of interest 512 has an intrusion defect 514 into a line 516. Summing columns of pixels for this region of interest produces a profile 518. This profile also has a flat baseline 520 because the pixels are summed in columns perpendicular to the edge of line 516. The increase in intensity for profile 518 at 522 is caused by intrusion defect 514 which allows more flux to pass through, thus creating a greater intensity of light at defect 514 which creates a higher intensity 522 in profile 518.

FIG. 11C shows a process 520 in which a region of interest 522 has an extension defect 524 on a line 526. Summing columns of pixels for this region results in a profile 528 having a lower intensity in region 529 due to defect 524. It should be appreciated that developing a profile for other defects such as a hole defect, and for other features such as line widths may be performed in a similar manner.

FIGS. 12A–12D illustrate examples of profiles that may be developed for a spot defect using the regions of interest shown in FIGS. 10A–10D, respectively. FIGS. 12A–12D show profiles 530, 540, 550 and 560, that have widely varying intensity distribution profiles for their corresponding regions of interest. Only profile 540 of FIG. 12B has a high quality profile in which the baseline 541 is flat and the feature region 542 of the profile will be proportional to the area of the feature. These varying profile results illustrate how multiple regions of interest can be used to find a high quality profile. Certain regions of interest may produce a poor profile, while others may produce a good profile. Thus, the use of multiple regions is advantageous. The development of statistics for each profile in order to find the best profile will be explained below with reference to FIGS. 8C and 8D.

Once an intensity distribution profile has been formed for a region of interest, in step 426 this profile is added to a profile list for later reference. Control then returns to step 420 and other profiles are developed for the remaining regions of interest. Once profiles have been developed for each of these regions of interest, the quality of the profiles can be evaluated by developing profile statistics.

Figure 8C:
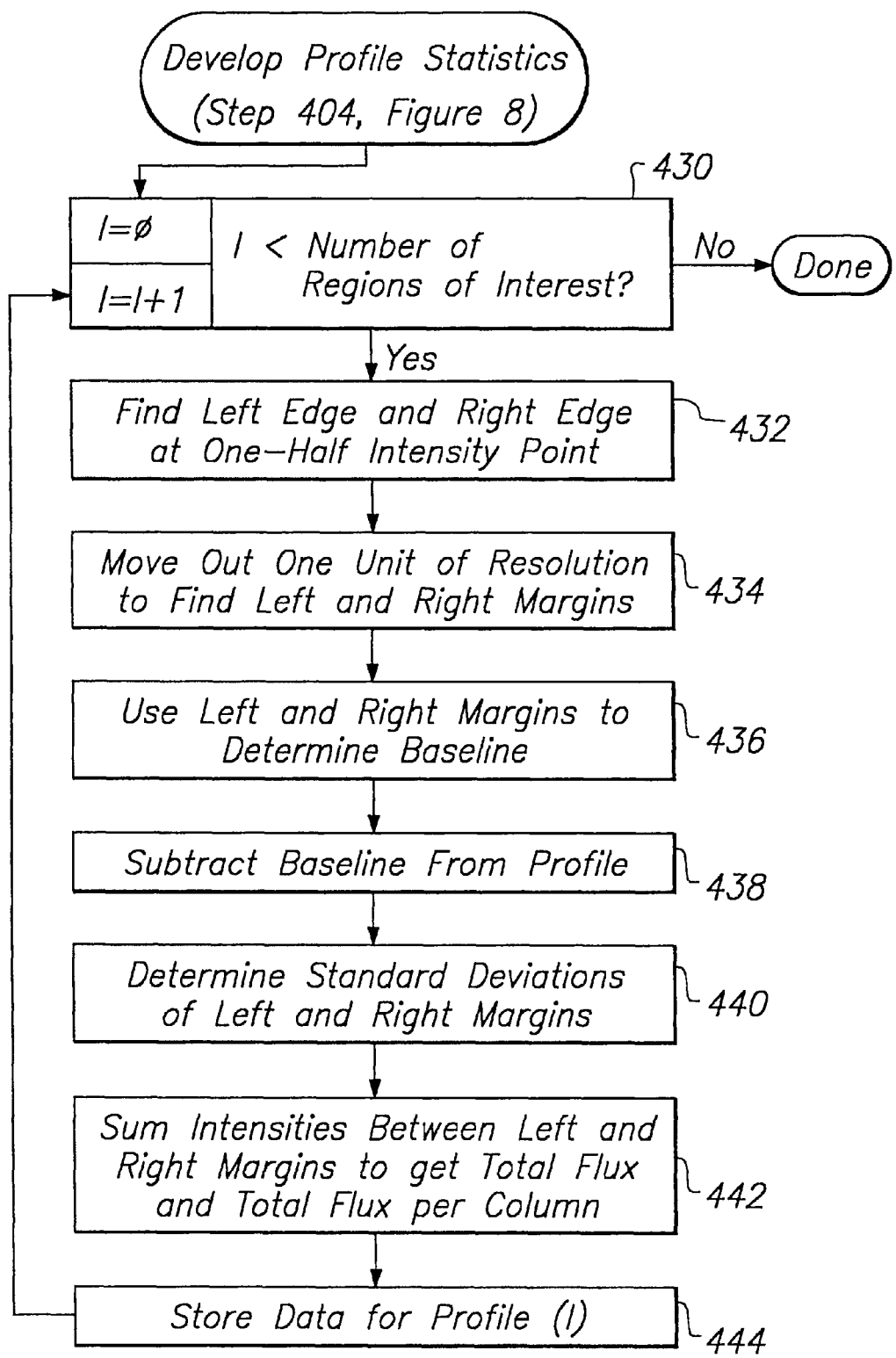
FIG. 8C is a flowchart for the develop profile statistics step of FIG. 8.

Development of profile statistics will now be explained with reference to FIG. 8C and FIG. 13. FIG. 8C is a flowchart illustrating a technique for the development of profile statistics. FIG. 13 shows in greater detail an intensity distribution profile 600, similar to either of the profiles of FIG. 11A or FIG. 12B. Profile 600 has been formed from a particular region of interest surrounding a spot defect or extension defect. It should be appreciated that profile 600 is an example of a profile and that various feature types may result in profiles of different forms. Profile 600 is plotted on a graph having an intensity axis 602 and a distance axis 604. Profile 600 has a feature region 606 containing the summed intensities of the pixels for particular columns within the feature to be measured. Profile 600 also has a baseline 608 and left and right margin portions 610 and 612.

Returning now to FIG. 8C, a technique for developing profile statistics will now be described. Step 430 loops through each of the profiles developed for each region of interest. Once statistics have been developed for all profiles then step 404 is done.

In developing profile statistics the use of a unit of resolution for the optics being used is helpful. In one embodiment of the invention, a Blur Size is determined empirically to estimate the resolution unit. In one embodiment, the Blur Size may be empirically determined as follows. Using a good quality profile having a fairly horizontal baseline, measurements are taken at 20% of the maximum intensity 630 and at 80% of the maximum intensity 634. The number of pixels located horizontally within the range bounded by the 20% and the 80% values is determined to be the Blur Size 636 which is an estimate of the resolution unit. This is a valid approximation of a resolution unit because were the optics to be perfect and everything to be in sharp focus, the intensity would not drop off gradually from maximum to zero but would transition immediately. Thus, since blurring causes a gradual drop off of intensity, a measurement of a Blur Size from 20% to 80% of intensity is a reasonable estimation of the resolution unit. Of course, other values and techniques may also be used in order to determine a resolution unit.

In step 432 the left edge 620 and the right edge 622 of profile 600 are determined by finding these corresponding points at the one-half maximum intensity level 624. Next, in step 434 a distance equal to one resolution unit 640 and 642 is measured from the left edge 620 and from the right edge 622 respectively, in order to determine an edge of the left margin 644 and an edge of the right margin 646. The corresponding outer edges 648 and 650 of the left and right margins respectively, are determined by finding points 652 and 654 at 5% of the maximum intensity 626, respectively, of profile 600.

Once the left margin portion 610 and the right margin portion 612 have been defined by locating their respective edges, the average of the intensity values along these two margins is used to form a baseline intensity 608 in step 436. Next, in step 438 baseline intensity 608 is subtracted from profile 600 in order to leave only feature region 606. Subtracting the baseline has a similar effect as step 270 of FIG. 7, in that background material is subtracted out. That is, the intensity values not due to the presence of a feature are removed. The advantage of subtracting a baseline is that no reference image need be obtained. More specifically, subtraction of a baseline accommodates for uneven illumination or slight rotation between the lines on the mask and the region of interest. These cause the baseline to be tilted but straight. After baseline subtraction, the margins yield a low standard deviation as described in the following paragraph.

In step 440, the standard deviations for the left and right margin intensities are determined in order to give an indication as to how flat the baseline is, which in turn indicates whether the profile is of good quality and would return an accurate flux reading. For example, a low standard deviation indicates a good baseline, while excess noise in the data would cause data points to have a larger deviation from the mean and result in a poorer baseline. In step 442 the intensities between edge 644 of the left margin and edge 646 of the right margin are summed in order to compute the total flux that passes through the feature. This total flux can then be used to determine the area of the feature or other dimensions.

The total flux is also computed to assist in determining the height of the feature or its line width. For line width, the total flux yields the area for the region of interest, which corresponds an area of a portion of the line to be measured. For example, FIG. 10E shows an area 395 of line 392. If the total flux is determined, this yields the value for area 395. Dividing this area value by the ROI height 391 yields the line width 394.

Height of a feature can also be determined from the total flux of one column of the profile. Dividing the total flux by the intensity range yields the area of that column. If an assumption is made that the defect is opaque (or totally clear), then the area of that column leads to a height measurement because the column is one pixel wide. Thus, the height is equivalent to the area.

Once the flux and the standard deviation have been computed for the profile, this data for the profile is stored for later reference in step 444. Control then returns to step 430 in which statistics are developed for any remaining profiles.

Figure 8D:
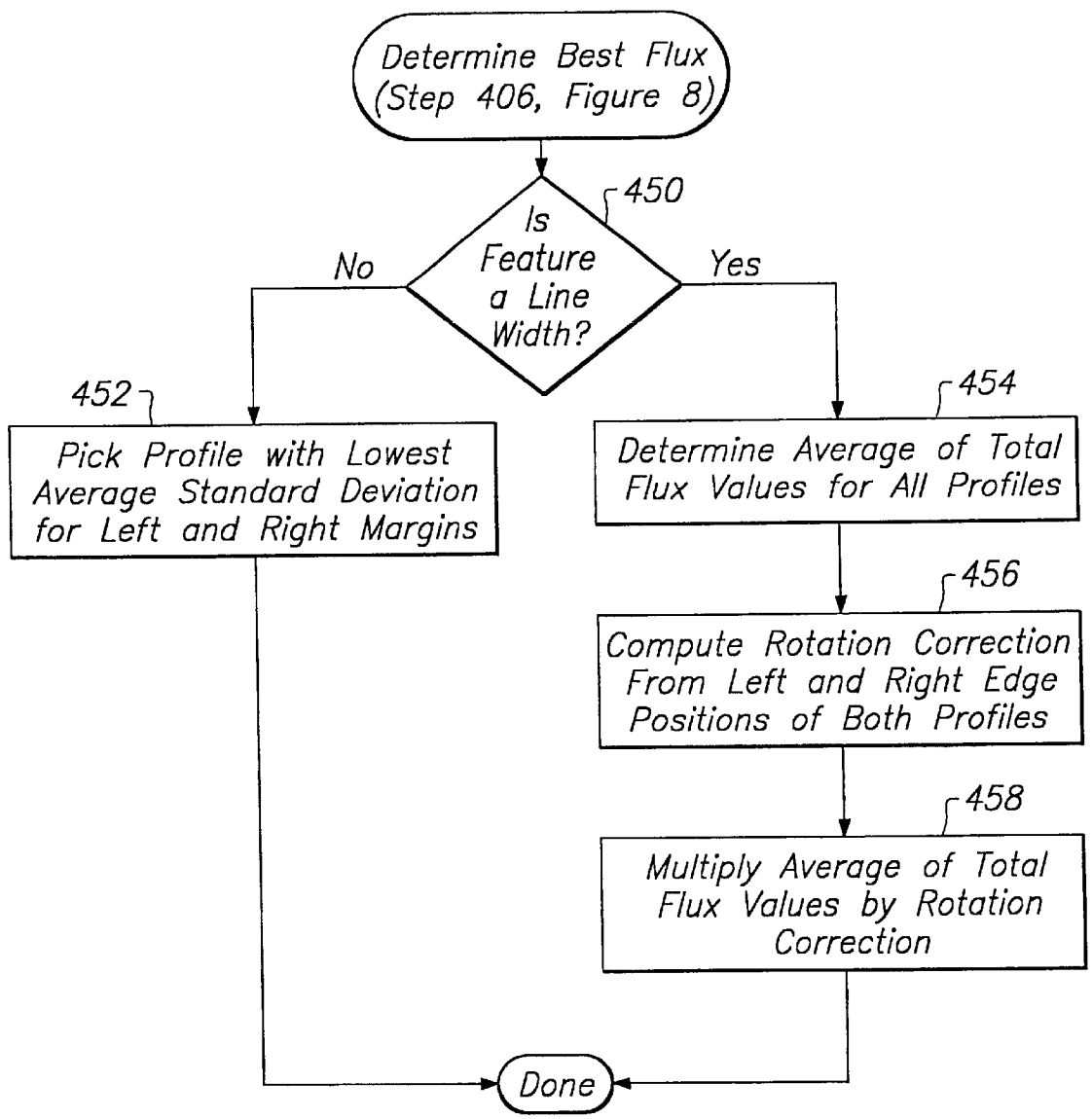
FIG. 8D is a flowchart for the determine best flux step of FIG. 8.

FIG. 8D illustrates an embodiment of the determine best flux step of FIG. 8. The best flux measurement will be determined by reference to the profile statistics developed for each profile in FIG. 8C. Step 450 determines whether the feature is a defect or line width. If the feature is a defect, then the profile with the lowest average standard deviation for the left and right margins is picked and the total flux measurement associated with that profile is returned to FIG. 6 as the determined flux for the defect. Only one of the profiles is picked in step 452 because only the profile with the lowest standard deviation for the margins will have the best and most accurate flux measurement for the defect. That is, only the best profile will have a total flux measurement that is proportional to the area of the defect.

As can be seen with reference to FIGS. 12A through 12D, various orientations for regions of interest produce wildly varying profiles. Since profile 540 of FIG. 12B (for example) has a relatively flat baseline 541, the average standard deviation for its left and right margins will be extremely low, indicating that this profile provides a feature region 542 having a flux measurement that most accurately reflects the flux passing through or being blocked by the defect. Once this profile and flux are determined in step 452, step 406 is done.

On the other hand, if the feature is a line width, then in step 454 the average of the total flux values for all profiles is determined. In step 454 the average of the total flux values is determined instead of picking a profile with the lowest standard deviation because the two regions of interest produced for a line width (as shown in FIG. 10E) are both at the same angle to the line and will produce nearly similar profiles and total flux values. In step 456 a rotation correction is computed from the left and right edge positions of both profiles in order to compensate for a line that may be angled. This rotation correction may be performed in a wide variety of manners. By way of example, the following formulas may be used:

theta=fabs(atan*2(Measured Center Difference, ROI Spacing Distance))

theta correction=cosine(theta)

where Measured Center Difference is the difference between the left hand edge positions of the profiles for each region of interest and ROI Spacing Distance is the distance in pixels between the two regions of interest.

Next, in step 458 the computed rotation correction (theta correction) is multiplied by the average of the total flux values in order to determine the correct flux measurement for the measured line width. Step 406 is then done.

Radius of Curvature General Background

An embodiment of the present invention is also useful in determining the radius of curvature of a corner of a feature on a photographic mask. In general, this embodiment is useful for determining the radius of curvature of any corner of a wide variety of media, and is especially useful where the size of radius involved approaches, or is less than, about the resolution of the microscope.

In the process of manufacturing photomasks and other such products, the sharpness of feature corners is a useful indicator of the quality of the process. Generally sharper (lower radius) corners indicate better focus and process control. Thus measurement of corner rounding is commonly used for process control in manufacturing photomasks.

Presently corner rounding is measured by receiving an image of a corner at a known high magnification, and then overlaying templates with circles of different radii. The template circle that appears to match the corner best gives the radius of the corner after correction for the image's magnification.

Unfortunately, the small geometries now used in photomasks make these measurements difficult because light microscopes, which are preferred for their ease of use and speed, do not allow measurement of radii smaller than about 0.25 micron. Any corner, no matter how sharp, will appear to have a radius of 0.25 micron (or about one-half the resolution of the microscope). Instead, measurements are taken with higher resolution microscopes such as scanning electron microscopes (SEM), Focused Ion Beam (FIB) microscopes, Atomic Force Microscopes (AFM), or light microscopes using UV illumination. These methods tend to be expensive, slow, complicated, and are unsuitable for a production environment. Accordingly, it would be desirable to have a technique for accurate measurements of a corner radius with a size less than about the resolution of the microscope that is fast, inexpensive and suitable for a production environment.

Radius of Curvature Description

The method discussed herein can use conventional optical microscopes or imaging methods that provide a "bright field", or "dark field" image. As shown in FIGS. 17 and 18, the basic technique is to compute the flux area of a region 920 that includes a perfect (zero radius) corner 918, subtract the flux area of the corresponding region 922 containing the actual corner 923, and then compute the radius 924 from that difference.

In another embodiment, the flux area of a region that includes a reference corner of known radius is computed. This flux area is then subtracted from the flux area of the corresponding region 922 containing the actual corner 923 to compute the radius 924 from that difference. Thus, steps 5–7 below of generating a reference corner would not need to be performed. Step 10 below would then be modified to determine the radius of curvature based on the flux area difference given that the reference corner has a known radius. For example, Radius=sqrt (4A/pi+(Radius of reference corner)^2).

Figure 22:
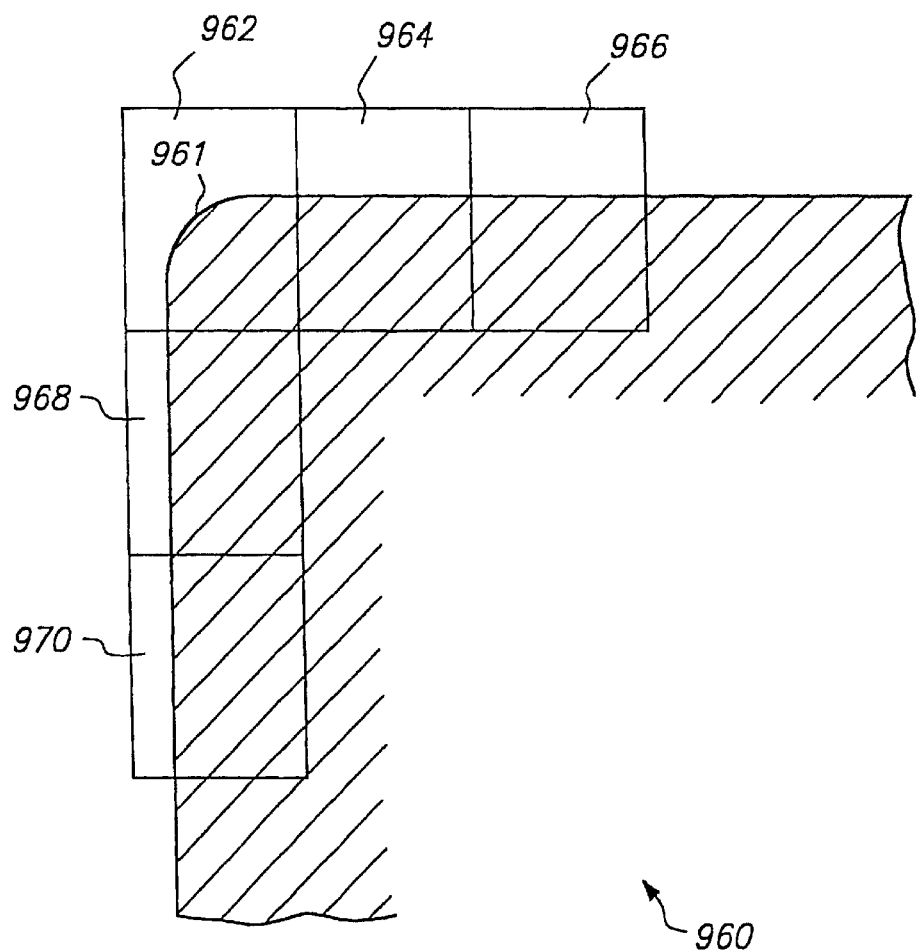
FIG. 22 illustrates an alternative embodiment for determining the radius of a corner.

An advantageous step is estimating the flux area of a perfect corner using the edges adjacent to it. For example, as shown in FIG. 22, this may be performed by replacing the corner region 962 with pixels or profile data extrapolated from data from the edge regions 964–970 suitably far from the corner (typically two blur distances). In a preferred implementation below this extrapolation is performed in steps 5 through 7.

The preferred implementation generates a reference profile for the corner region 962 of FIG. 22 by extrapolating and multiplying the profiles from regions 964–970 to produce a Corner Reference Profile, subtracting the measured profile for the corner region from the Corner Reference Profile, and computing the corner radius that would produce that flux difference.

Figure 19:
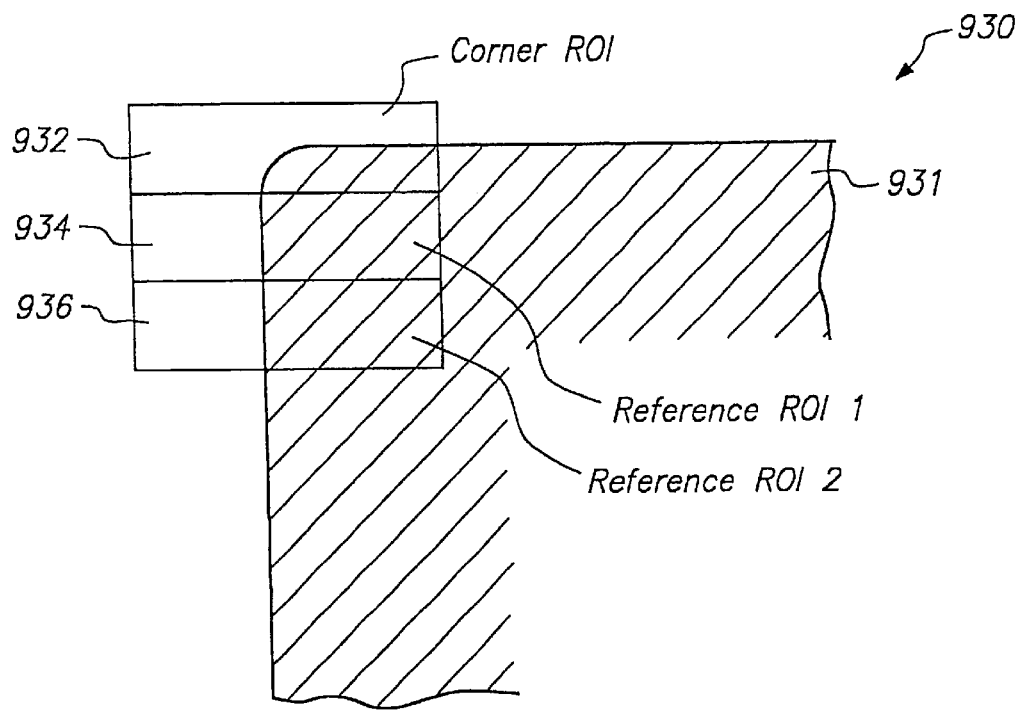
FIG. 19 illustrates regions of interest useful in determining the radius of a corner.

An embodiment uses the following steps to calculate the radius of curvature. A step 1 digitizes an image of the corner to be measured. Step 2 rotates the image so that the corner direction is as shown in FIG. 19. This can also be accomplished by suitable arrangement of the regions of interest (ROIs) described below. The rotation can be in increments of 90 degrees or fractional degrees. Step 3 defines three ROIs. One is the Corner ROI 932 with a width of 6 blur distances, a height of 4 blur distances, and a position of upper left corner being two blur distances above and left of the corner in the image. This position can be determined by the operator or with standard edge finding techniques. Two other ROIs are Reference ROIs 1 and 2, 934 and 936. Each has a size the same as Corner ROI and a position stacked below and adjacent to the Corner ROI.

Figure 20:
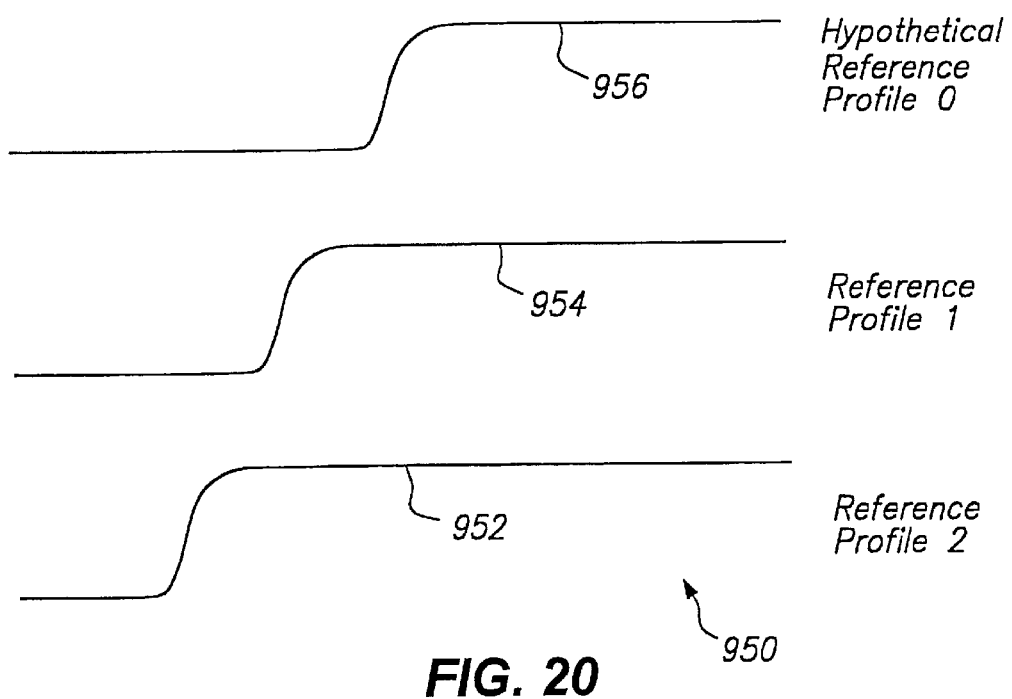
FIG. 20 illustrates profiles developed from the regions associated with a corner.
Figure 21:
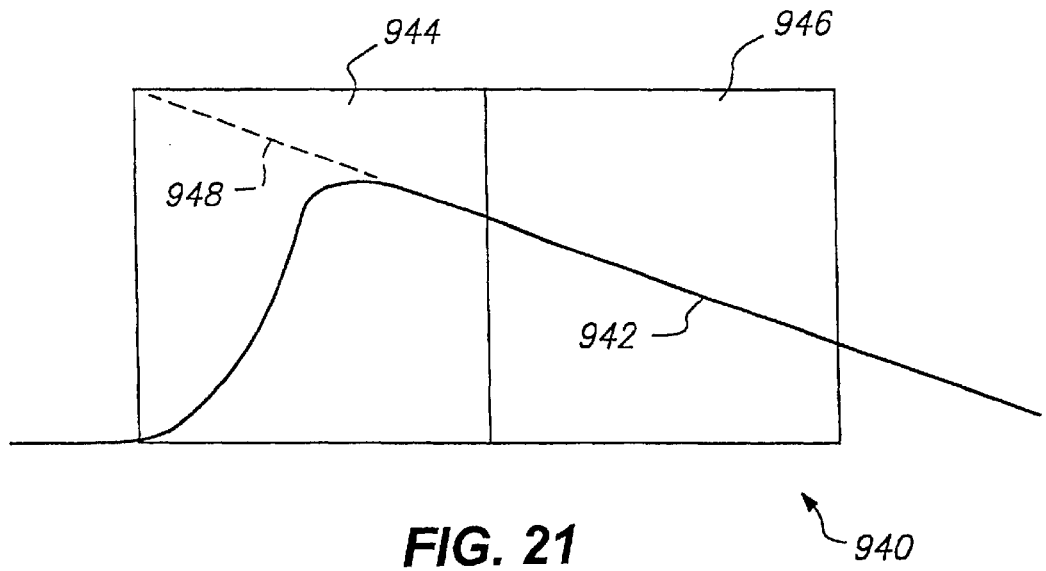
FIG. 21 illustrates another profile associated with a corner.

Step 4 takes intensity profiles of the three ROIs shown in FIG. 19. This produces the Corner Profile (FIG. 21, 942) and two Reference Profiles. As shown in FIG. 20, step 5 computes the hypothetical reference profile 0 956 which corrects the reference profile 1 954 left or right for any deviation of the vertical edge from vertical. (If the vertical edge is known to be exactly vertical this step can be skipped and reference profile 1 954 is copied into hypothetical reference profile 0 956. More specifically this step computes the subpixel 50% threshold crossing position of reference profiles 1 and 2, 954 and 952. Then it shifts reference profile 1 left or right by the fractional pixel shift between profiles 2 and 1. Thus, it gives the vertical edge profile expected in the Corner ROI.

Step 6 normalizes the hypothetical reference profile values to between 0 and 1 so that they represent the Vertical Edge Attenuation Profile. Step 7 creates a Corner Reference Profile (for a zero-radius corner) which is corrected for the slopes of the two edges as follows: divide the Corner Profile 942 into two parts (FIG. 21); replace the left side 944 (which is four blur distances wide) with a linear extrapolation of the right side 946 (which can be two blur distances wide). This describes the horizontal edge 948 expected without the corner. Multiply the resultant profile 948 by the Vertical Edge Attenuation Profile (956 normalized) from step 6, giving the Corner Reference Profile.

Step 8 subtracts the Corner Profile 942 from the Corner Reference Profile, and sums the differences to get the total flux difference. Alternatively, the total flux could be computed for each profile and the fluxes subtracted to produce the total flux difference. Step 9 normalizes the total flux difference to the image's contrast range as described earlier herein to get the flux area difference (with units of square pixels).

Step 10 computes the radius of curvature that would give that flux area difference by finding the radius of the circle where the difference in area between the circle and its enclosing square equals the flux area difference times four (because only one of four corners of the square is measured here). For example, radius=sqrt(A(1-pi/4)) (where A is the flux area difference in pixels, and radius is the corner radius in pixels).

Step 11 scales the Corner Radius from pixels to physical units such as microns using a simple scale factor measured or computed based on the optical system, or by using a calibration curve as described earlier herein based on reference measurements derived externally.

An alternate method to compute a radius of curvature is to compute the edge equations (Y=mX+b) for the horizontal and vertical edges from the "50%" threshold intersections in regions 964, 966, 968, and 970. From these equations generate a binary image representing a perfect zero radius corner. Then subtract the measured image or profile of the corner region 962 from this reference image or profile of it and sum the flux differences from all the pixels. Finally, continue with step 9 above to compute the flux area, radius in pixels, and radius in physical units.

An advantageous step in this alternate method is determining the actual threshold to use, because the threshold should correspond to 50% energy (the integral of the normalized intensity across the edge), not 50% intensity. If the blurring is symmetrical, these values will be identical, but if it is not, the intensity corresponding to 50% energy could be computed in several ways.

By way of example, one method is to compute the integral of the normalized intensities across the edge and pick the position where it crosses 50%, and then interpolate the edge intensity values to that position. This can also be done iteratively as follows: start with a simple 50% threshold, compute the edge position, generate a binary image of the region with that edge position, and compare the total flux in that region with the total flux in the normalized measured image. Then adjust the threshold slightly until the measured image and the binary image have the same total flux.

In another embodiment described below in FIGS. 23 and 24, a different, simpler technique is used to determine corner radius. The above more complicated method is preferred because it produces a difference image which is used as a diagnostic to visually verify that the algorithm had been applied correctly. The primary causes of failure are 1) the horizontal and vertical profiles not being on representative straight edges, 2) there may not be any straight edges (e.g., on a quasi-circular feature), and 3) other edges are too close to the corner being measured. In these cases, the difference image would not look like a rounded corner and the user would be alerted.

Figure 23:
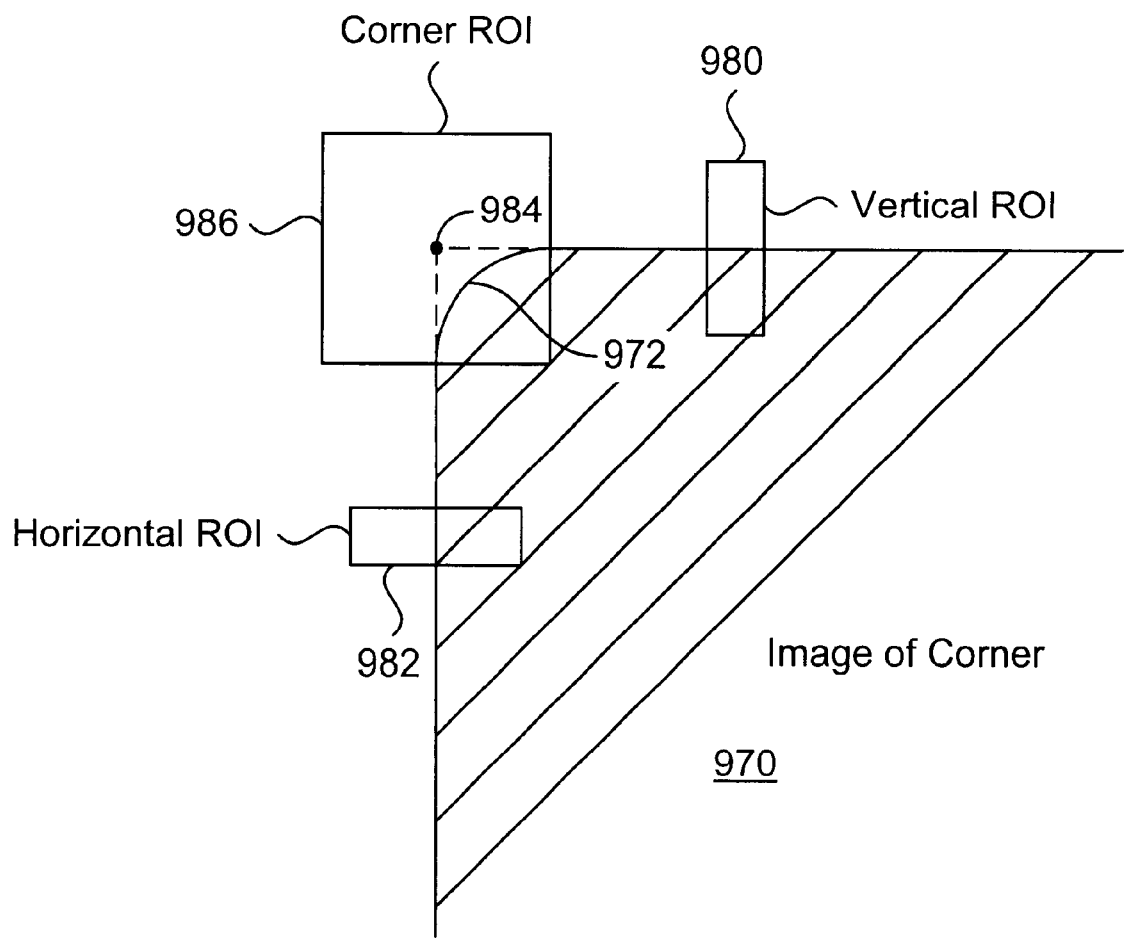
FIG. 23 illustrates an image of a corner of a feature on a photomask, and another embodiment for determining the radius of a corner.

FIG. 23 illustrates an image of a corner of a feature on a photomask. Corner image 970 has a rounded corner 972; were it a perfect corner, the corner would be located at point 984. It is desired to determine the corner radius of the feature; the feature may be a corner of a line, any inside or outside corner, or anything that has a 90 degree (or approximately 90 degree) corner. Preferably, the lines defining the corner are longer than one blur distance; any shorter and the radius becomes undefined. The following technique is simpler in that it eliminates production of the corner reference profile and the production of the difference image.

This technique describes the corner reference image (an image of a projected perfect corner) with three values: the dark level (intensity), the bright level (intensity) and the exact corner using determined X and Y coordinates. From these values we can calculate the total expected flux in the corner region of interest (corner ROI) for the perfect corner, and compare that to the actual total flux in the corner ROI of the sample image.

More specifically, the technique operates as follows. In a first step a vertical ROI 980 and a horizontal ROI 982 are defined roughly crossing over the boundaries of the image as shown. These regions are defined as explained earlier, and preferably their sizes are as explained in FIG. 19.

In a second step, the 50% threshold position (fractional pixel) is determined in each of the vertical and horizontal profiles. This 50% threshold position is the point at which the intensity is 50% across the ROI, and corresponds to the point where the edge of the corner is. Calculation of the position for the vertical profile yields an X value and the position for the horizontal profile yields a Y value, as if the image were superimposed on an infinitely fine grid.

These two positions of the two profiles define an X and a Y position that define where the perfect corner 984 would be located as the edges of the image are extrapolated to position 984. Position 984 is used to define the location of the perfect corner, and hence an area for region 988 which is used to calculate the flux when a perfect corner is present. In a third step, we next define a corner ROI 986 around that perfect corner position. Preferably, the size of this corner ROI is approximately 4×4 blur distances Preferably, first rough calculations for the X and Y positions of the edges of the corner are calculated, and Corner ROI 986 is located roughly centered over where the perfect corner would be. These rough calculations preferably take place before vertical and horizontal ROIs 980 and 982 are used to precisely define an X and a Y position for the perfect corner.

Figure 24:
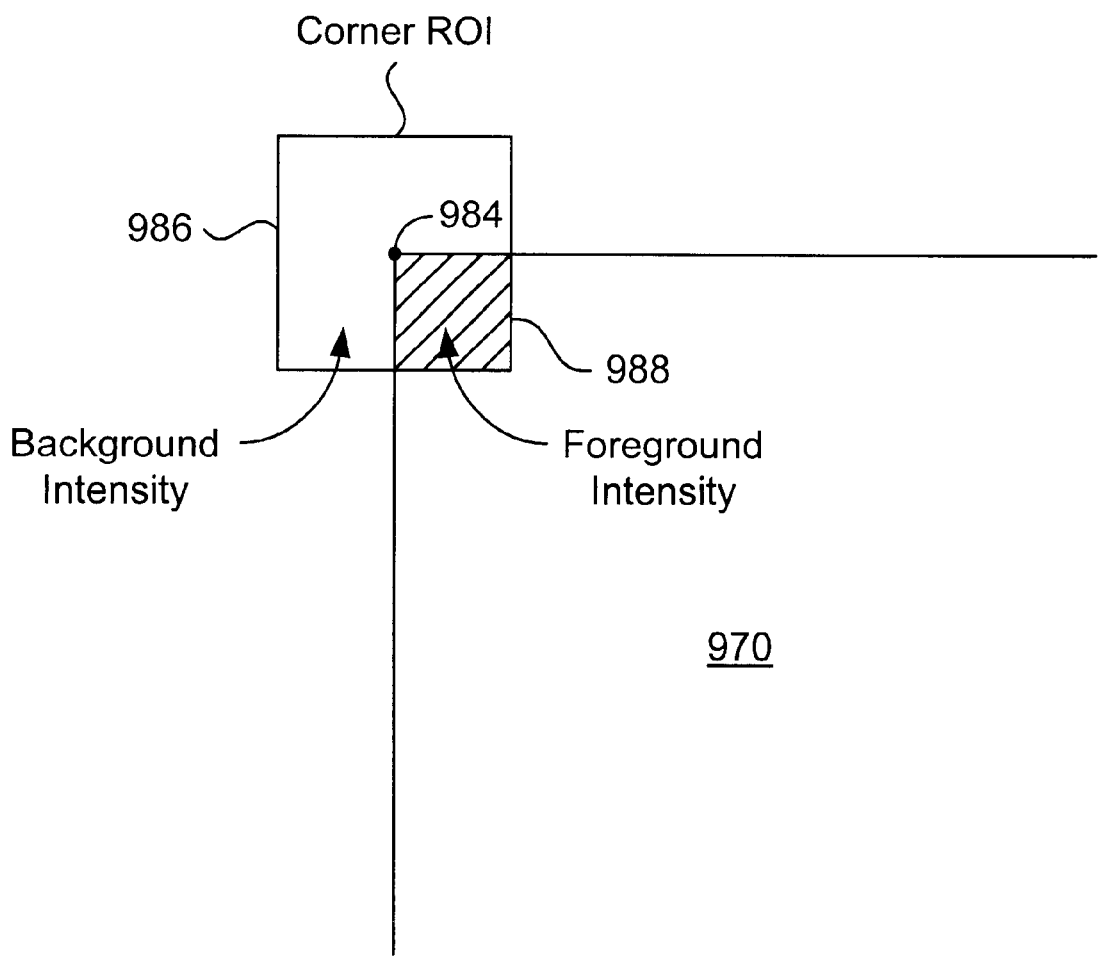
FIG. 24 illustrates an image of a projected corner of the actual corner of FIG. 23.

FIG. 24 illustrates an image of a projected perfect corner of the actual corner of FIG. 23. Corner area 988 is that region of the corner that falls within the corner ROI. The background intensity refers to the intensity of the region outside the corner, while the foreground intensity refers to the intensity of the region of the corner.

In a fourth step, we calculate the expected total flux inside the corner ROI assuming the corner were perfect, taking into account the background and foreground intensities. These intensity of the background and foreground may be calculated as previously described in FIGS. 7 and 7A. Of course, the foreground may be the dark level and the background the bright level, or vice-versa.

The expected total flux (of a perfect, unrounded corner) in the Corner ROI is calculated based on the dark and bright intensities described in FIG. 7A and the corner X and Y determined from the subpixel threshold positions above. First "foreground" and "background" intensities are assigned. For example, if the corner is dark then the foreground intensity is the dark intensity and the background intensity is the bright intensity. Conversely, if the corner is bright, then the foreground is the bright intensity and the background is the dark intensity.

Next the area of the perfect corner 988 "Corner_Area" is simply calculated from the corner position 984 and the position of the Corner ROI 986 as shown in FIG. 24. Finally the expected total flux is determined by adding the background flux and foreground flux:

Expected_Total_Flux=(Corner_ROI_Area−Corner_Area)*Background_Intensity+Corner_Area*Foreground_Intensity Finally, the expected total flux of the corner ROI is subtracted from the actual total flux. The actual total flux is calculated as described above and is the sum of all pixel values in the corner ROI. The result is the flux associated with the corner rounding (an "eroded area" flux), from which may be calculated the radius of curvature. Preferably, calculation of the radius from the flux first involves normalizing the flux to the image's contrast range to get the flux difference in units of square pixels. The radius of curvature that would give that flux area difference is computed by finding the radius of the circle where the difference in area between the circle and its enclosing square equals the flux area difference times four (because only one of four corners of the square is measured here). For example, radius=sqrt (A(1−pi/4)) (where A is the flux area difference in pixels, and radius is the corner radius in pixels).

Next, the corner radius is scaled from pixels to physical units such as microns using a simple scale factor measured or computed based on the optical system, or by using a calibration curve as described earlier herein based on reference measurements derived externally.

Illumination and Inspection Embodiments

The present invention is useful in conjunction with a wide variety of lighting sources and/or particle microscopes (such as an electron microscope). Considering lighting sources first, it is known in the art to use transmitted illumination, bright field illumination (also called axial illumination), and dark field illumination (also called oblique illumination) to illuminate a medium. Other similar lighting techniques may also be used and the present invention can be used with any of these lighting techniques. For example, it may be desirable to use one of the above lighting techniques on a video inspection machine for inspecting a surface for particulate matter, features, defects and/or line widths. In fact, certain inspection machines are able to employ more than one lighting technique simultaneously, thereby aiding the operator in identifying and sizing particles and features. Because a particular particle or feature may appear best under a certain type of lighting, it can be advantageous to employ more than one lighting technique.

As mentioned above, one lighting technique applicable for use with the present invention is transmitted illumination. Using this technique, light is transmitted through a medium under inspection in order to identify and size various types of features. The transmitted illumination technique is most useful for transparent media because the transparent media will not completely block all of the transmitted light. Media that are suitable for use with transmitted illumination include glass reticles, semiconductor masks, etc., and other transparent media and semi-transparent media. By using transmitted illumination, different features may appear dark or bright. Whereas a spot defect, a chrome line or other opaque substance would appear dark, a hole or absence of a portion of a chrome line on a glass reticle would appear bright because the transmitted light is allowed to pass through the transparent medium.

Another lighting technique is bright field illumination. Unlike transmitted illumination, bright field illumination uses a lighting source that is directed on to, and thus reflected from, the medium under analysis. In a typical setup, a light source is located perpendicular to the lens axis and the light is directed onto the medium axially by way of a reflecting mirror. A camera or other sensing device then picks up the light reflected from the medium. Bright field illumination is advantageous for an opaque surface such as a silicon wafer or other material. For completely or nearly opaque media, transmitted illumination would not be particularly useful because the light would not be transmitted; thus, bright field illumination that uses reflected light can be more advantageous. In addition, bright field illumination may be used with transparent media such as glass, a semiconductor mask or other because such a material, even though able to transmit light, will also reflect light. In general, any reflective medium is suitable for analysis using bright field illumination. In particular, bright field illumination is useful for identifying and sizing excess chrome, dirt or other particulate matter on silicon wafers, chrome surfaces, etc.

With bright field illumination flat surfaces appear bright because they reflect light, while a surface, particle or feature more or less not flat will appear dark because it does not allow light to be reflected back to a sensing device. For example, with bright field illumination spot defects, holes, chrome lines, line extensions, etc. will appear dark, while a flat surface or a missing portion of a chrome line would appear bright. In general, any feature or defect of about less than one micron in size will appear dark because such a feature or defect is close to the wavelength of light. Anything that small would not necessarily appear flat, and thus would appear dark.

Another lighting technique suitable for use with the present invention is dark field illumination. In dark field illumination a lighting source is typically located at an oblique angle from the medium under analysis. In a typical setup, a circular fluorescent light encircles the lens and medium under analysis and provides lighting from the side. As the lighting is from the side, the flat medium will appear dark because it does not necessarily reflect light directly into the lens. However, spot defects, holes, chrome lines, line extensions, etc. will often appear brighter than the dark background because their curved or rough shape allows a certain amount of light to be reflected back up into the lens. For example, a hole or other indent in a flat medium such as a silicon wafer may appear bright, whereas the flat wafer itself would appear dark.

The various embodiments of the inventions described herein are also suitable for use with a variety of particle microscopes such as an electron microscope or a focused ion beam (FIB) microscope. Thus, although many references to light measurements are made herein, and many of the measurements and units are applicable to visible light, the invention is not so limited. References have been made to visible light measurements for ease of presenting the invention. The techniques of the present invention are also applicable to measurements made with other particles as well as electrons. Therefore, references to "wavelength" refer to light wavelengths, electron wavelengths, or wavelengths of other particles used for measurement.

Computer System Embodiment

Figure 25A:
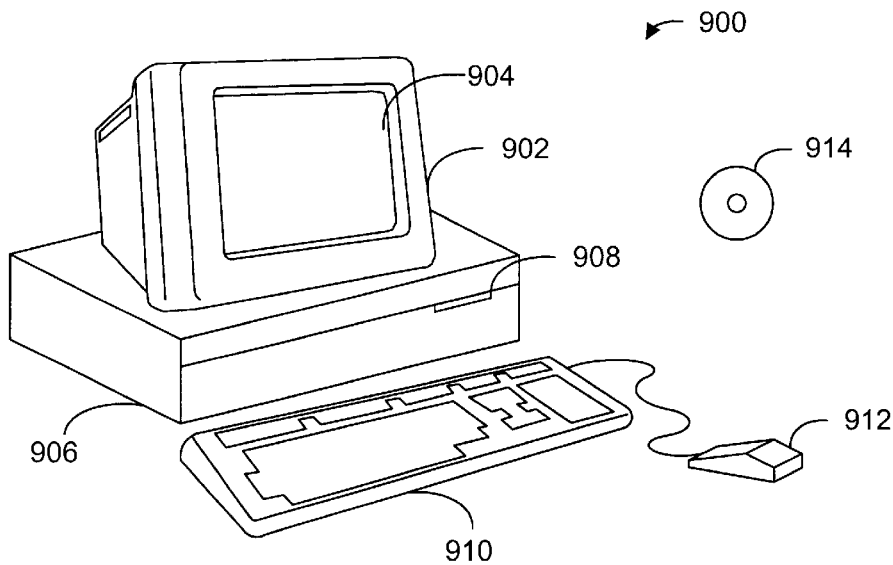
FIGS. 25A and 25B are a block diagram of a typical computer system suitable for implementing an embodiment of the present invention.
Figure 25B:
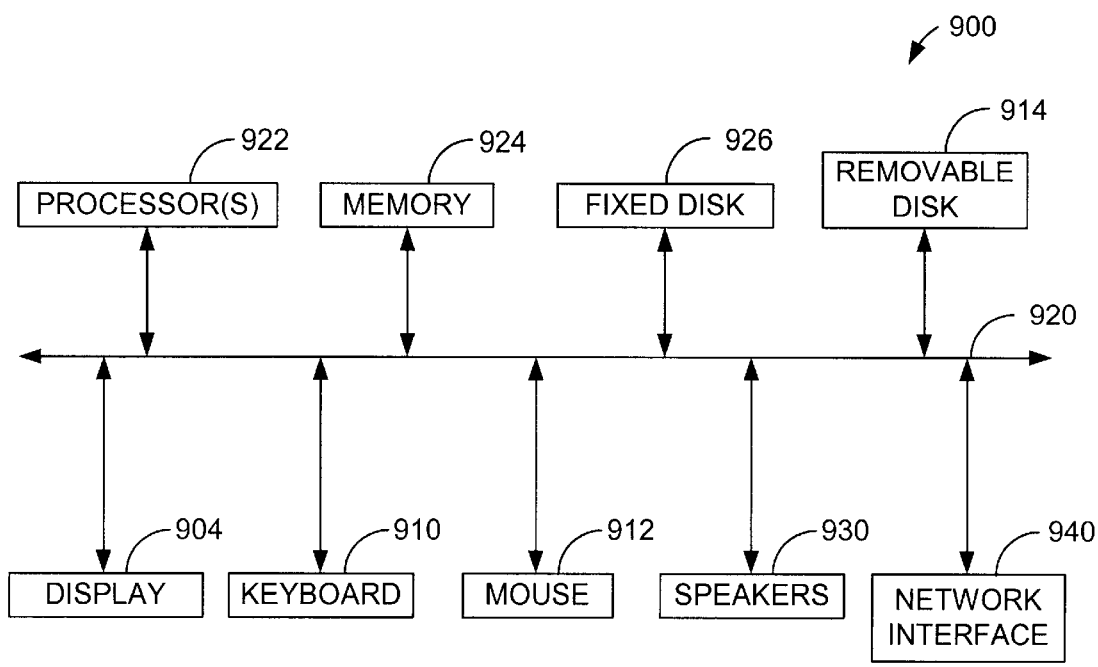

FIGS. 25A and 25B illustrate a computer system 900 suitable for implementing embodiments of the present invention. FIG. 25A shows one possible physical form of the computer system. Of course, the computer system may have many physical forms ranging from an integrated circuit, a printed circuit board and a small handheld device up to a huge super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 25B is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary storage medium (such as a hard disk) that is slower than primary storage. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps.

Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

Although the foregoing invention has been described in some detail for purposes of clarity of understanding, it will be apparent that certain changes and modifications may be practiced within the scope of the appended claims. For instance, the video image input may come from a wide variety of sources. Also, measurements may be taken of a variety of features at the micron level that are present on a variety of media, and not necessarily a photomask. For example, the invention is applicable to biological specimens such as cells, etc. Also, any type of light microscopic may be used as well as an electron microscope or other particle microscope. In addition, the present invention is applicable to measuring a wide variety of features including contacts, vias or other intentional features. Therefore, the described embodiments should be taken as illustrative and not restrictive, and the invention should not be limited to the details given herein but should be defined by the following claims and their full scope of equivalents.

I claim:

1. A method of determining the radius of curvature of a microscopic corner feature located on a medium, said method comprising:

determining the location of the perfect corner of said corner feature;

calculating an expected flux value for a region of interest around said corner feature assuming that said corner feature were the perfect corner;

calculating an actual flux value for said corner region of interest around said corner feature;

calculating an eroded area flux value from said expected flux value and said actual flux value; and calculating the radius of curvature of said corner feature using said eroded area flux value.

2. A method as recited in claim 1 wherein said radius of curvature is less than about twice the wavelength used in said method.

3. A method as recited in claim 1 wherein said step of determining the location of the perfect corner includes the sub-steps of:

defining a vertical and a horizontal region of interest across edges that define said corner feature; and determining an X-Y coordinate position for said location of the perfect corner using said vertical and horizontal regions of interest.

4. A method as recited in claim 1 further comprising:

defining said corner region of interest around said corner feature using rough approximations for the X-Y coordinate positions of said perfect corner location.

5. A method as recited in claim 1 wherein said step of calculating an expected flux value includes the sub-step of:

calculating an expected flux value for said region of interest around said corner feature using a background intensity and a foreground intensity of said corner region of interest.

6. A computer-readable medium comprising computer code for determining the radius of curvature of a microscopic corner feature located on a medium, said computer code of said computer-readable medium effecting the following:

determining the location of the perfect corner of said corner feature;

calculating an expected flux value for a region of interest around said corner feature assuming that said corner feature were the perfect corner;

calculating an actual flux value for said corner region of interest around said corner feature;

calculating an eroded area flux value from said expected flux value and said actual flux value; and calculating the radius of curvature of said corner feature using said eroded area flux value.

7. A computer-readable medium as recited in claim 6 wherein said radius of curvature is less than about twice the wavelength used in said method.

8. A computer-readable medium as recited in claim 6 further comprising computer code for effecting the following:

defining a vertical and a horizontal region of interest across edges that define said corner feature; and determining an X-Y coordinate position for said location of the perfect corner using said vertical and horizontal regions of interest.

9. A computer-readable medium as recited in claim 6 further comprising computer code for effecting the following:

defining said corner region of interest around said corner feature using rough approximations for the X-Y coordinate positions of said perfect corner location.

10. A computer-readable medium as recited in claim 6 further comprising computer code for effecting the following:

calculating an expected flux value for said region of interest around said corner feature using a background intensity and a foreground intensity of said corner region of interest.

* * * * *